United States Patent [19]

Sussman et al.

[11] Patent Number: 5,368,555
[45] Date of Patent: Nov. 29, 1994

[54] ORGAN SUPPORT SYSTEM

[75] Inventors: Norman L. Sussman; James H. Kelly, both of Houston, Tex.; Donn D. Lobdell, Corona Del Mar, Calif.

[73] Assignee: Hepatix, Inc., Houston, Tex.

[21] Appl. No.: 998,146

[22] Filed: Dec. 29, 1992

[51] Int. Cl.⁵ ............................................. A61M 37/00
[52] U.S. Cl. ........................................... 604/4; 435/1; 435/283; 435/284
[58] Field of Search ........................................ 604/4–6, 604/173, 93; 623/11, 12; 435/1, 2, 283, 284, 285

[56] References Cited

U.S. PATENT DOCUMENTS

| | | |
|---|---|---|
| Re. 31,688 | 9/1984 | Popovich et al. |
| 4,209,392 | 6/1980 | Wallace |
| 4,299,705 | 11/1981 | Russell |
| 4,353,368 | 10/1982 | Slovak et al. |
| 4,464,167 | 8/1984 | Schoendorfer et al. |
| 4,568,327 | 2/1986 | Seufert |
| 4,648,866 | 3/1987 | Malbrancq et al. |
| 4,650,458 | 3/1987 | Dahlberg et al. |
| 4,657,529 | 4/1987 | Prince et al. |
| 4,853,324 | 8/1989 | Viles et al. ............... 604/4 |
| 4,897,185 | 1/1990 | Schuyler et al. |
| 4,925,555 | 5/1990 | Spielberg ................. 604/4 |
| 5,043,260 | 8/1991 | Jauregui .................. 604/4 |
| 5,078,885 | 1/1992 | Matsumura ............... 604/4 |
| 5,211,849 | 5/1993 | Kitaevich ................. 604/4 |
| 5,270,192 | 12/1993 | Li et al. .................. 435/174 |

OTHER PUBLICATIONS

Artif. Organs, vol. 16, No. 4, "Assessment of an Extracorporeal Liver Assist Device in Anhepatic Dogs", Kelly et al., Jan. 1992, pp. 418–422.
Hepatology, vol. 16, No. 1, "Reversal of Fulminant Hepatic Failure Using an Extracorporeal Liver Assist Device", Sussman et al., Jan. 1992, pp. 60–65.

Primary Examiner—C. Fred Rosenbaum
Assistant Examiner—Frank Wilkens, III
Attorney, Agent, or Firm—Sughrue, Mion, Zinn, Macpeak & Seas

[57] ABSTRACT

An organ support system and method adapted for use with a patient and designed to modify the blood from the patient includes a control system, a venous line coupled to an output of a patient, an arterial line coupled to an input of the patient, and a cell line inserted into a hollow fiber cartridge to form an organ assist device. Blood is passed through the organ assist device. A small flow is extracted from the extracapillary space to check the integrity of the organ assist device. With this closed loop arrangement, a proper fluid balance can be maintained for the patient without requiring any dialysate, and leaks from the cell line to the patient can be immediately detected and prevented from reaching the patient.

29 Claims, 11 Drawing Sheets

BLOOD CIRCUIT

ULTRAFILTRATE CIRCUIT

ORGAN SUPPORT SYSTEM

This application incorporates herein by reference U.S. Pat. application Ser. No. 07/524,075, filed on May 16, 1991, U.S. Pat. application Ser. No. 07/965,448 (the continuation-in-part of U.S. Pat. application Ser. No. 07/524,075), filed on Oct. 23, 1992, and PCT Publication No. WO 91/18087.

The present invention relates to an organ support system and method for sustaining a patient, and more particularly to an organ support system having a cell line which mimics or supports the function of a specific bodily organ e.g., liver, kidney, etc. The embodiment of the invention discussed in detail below is directed to the liver, but it is envisioned that the support system can be used for other organs. The components of the system include a hollow fiber cartridge, biologically active cells which could be a continuously cultured cell line, and a pumping system.

Hollow Fiber Cartridges

Briefly, hollow fiber cartridges consist of a tube which contains a plurality of hollow fibers. The hollow fibers can be made of a number of substances such as polysulfone or cellulose acetate, and may vary in diameter. The cartridge has two spaces; an intracapillary space (ICS) and an extracapillary space (ECS). The ICS is the space comprised of the interior of the fibers, and is accessed through the end ports of the cartridge. The ECS is the space between the outside of the fibers and the shell of the cartridge, and is accessed through the side ports as shown, for example, in FIG. 1. These two spaces are the basis of hemodialysis; a continuous stream of blood passes through one space and is dialyzed against a continuous stream of fluid (i.e., a dialysate) which passes through the other space. The nature of the membrane dictates the type of exchange which takes place between these two streams, but transfer of water and small-to-medium-sized molecules is usually the goal. Blood is usually passed through the intracapillary space since flow is less turbulent, and clotting is reduced. The system would function in the reverse orientation, i.e., blood in the ECS, dialysate in the ICS. The description in this application refers to the conventional orientation of blood flow for convenience, but it is recognized that the system may work equally well in the reverse orientation.

BACKGROUND OF THE INVENTION

It is known that the acute loss of more than 60% of liver function is a serious risk to survival. It is also known that patients with chronic liver insufficiency may have periods when a metabolic stress such as surgery or an infection places them in liver failure. The liver serves to remove impurities from the blood and either recycles them to useful compounds, or converts them to harmless waste products which are excreted by the kidneys. Without a properly functioning liver, the body is unable to maintain its normal metabolic balance, and many organs cease to function because of the build-up of toxins or because the liver is no longer synthesizing important nutrients. The functions of the liver are not completely known, but are such that simple removal of toxins from the blood by hemodialysis or hemoperfusion does not alleviate the patient's condition. Removal of toxins by these methods may improve one or more aspects of the patient's condition such as acid-base balance or mental status, but the overall condition is unaffected, and mortality is not improved.

Even though the liver is the only organ capable of regeneration, severe liver failure does not provide the optimum metabolic circumstances for such regeneration to take place. Faced with a rapidly deteriorating patient, the only successful treatment to date has been the removal of the failing liver and transplantation with a donor liver. There are, however, several major concerns with liver transplantation including the procurement of a matching organ within a useful time frame, the transport of the organ to the patient, major surgery which carries a 10–20% mortality, the continuing danger of rejection of the transplanted organ, and the expenses involved in the operation and subsequent medical care of the patient.

In view of the foregoing concerns, potential uses for a liver support system include supporting a patient until recovery from a metabolic stress, sustaining a liver transplant candidate until a suitable organ is available, and supporting a patient after transplantation until the grafted liver is functioning adequately and can fully sustain the patient. The solution to the problem is a metabolically-active liver assist device, i.e., one containing functioning liver cells. Implementation of such a device raises several problems which have not previously been encountered in extracorporeal blood therapies. These problems include inter alia:

- The need for a continuous oxygen supply to maintain cell viability;
- The need to maintain a positive pressure gradient from the ICS to the ECS to prevent cells from migrating into the ICS in the event of a fiber rupture;
- The need to perfuse the ECS in order to reduce the concentration of clotting factors, thus reducing the likelihood of blood clotting in the cartridge;
- The need to monitor the fluid in the ECS to assess the continuing viability of cells in the ECS;
- The need to return fluid from the ECS to the patient's blood stream in order to supply proteins which are secreted by the cells; and
- The need to temporarily support the metabolic requirements of a cartridge while the need for further treatment is evaluated.

Extracorporeal Blood Therapies

A number of blood purification systems are available. In each instance, blood flow and control of the overall operation are of critical importance, and the pumping system has been designed to address the specific needs of the procedure. None of these conventional systems, however, addresses the specific needs outlined in the paragraph above. Their shortcomings are discussed below.

Hemodialysis

Hemodialysis is a form of extracorporeal blood treatment in which blood flows of up to 25% of the cardiac output are employed. It is by far the most widely practiced extracorporeal procedure involving about 100,000 patients and requiring about 15,000,000 treatments annually in the United States. The treatment has been routinely practiced for the past 25 years with an ever-expanding and longer surviving patient population. The most widely used form of hemodialysis is chronic intermittent hemodialysis (CIHD), in which the blood is purified by using a dialysate. Dialysate is a salt solution designed to promote diffusion of toxins from the patient to the dialysate while restoring salt and acid-base balance to the patient's blood. In CIHD, the patient's blood is exposed through a membrane to a considerable quantity of dialysate. In CIHD methods and apparatus, the dialysate is typically prepared on-line from salt concentrates and water. Typically, the water used in the dialysate is prepared by reverse osmosis. Since the dialysate is always separated from the blood stream by a semi-permeable membrane (which does not admit micro-organisms), it is neither necessarily sterile nor pyrogen-free. Thus, the fluid from the ECS cannot be recirculated to the patient's blood stream.

Conventional hemodialysis also requires careful management of fluid balance. One of the most important issues in hemodialysis is the control of ultrafiltration, the removal of excess fluid from the patient. Removal of excess fluid or insufficient fluid from the patient may be fatal. Hence, a considerable portion of conventional hemodialysis hardware and software systems is devoted to monitoring, controlling, and assuring appropriate patient fluid removal at all times.

Another shortcoming in conventional dialysis operations is that the conventional systems operate on a given patient for a period of about 4 hours. Continuous veno-venous hemodialysis (CVVHD) is a technique in which therapy is continuous for several days. However, CVVHD has the same shortcomings as CIHD; fluid, electrolyte, and acid-base balance are the goals as well as the source of greatest concern in terms of side effects, and the fluid from the ECS cannot be returned to the patient's blood stream.

Yet another shortcoming is the inability of existing hardware to sustain a metabolically-active device once blood flow is diverted from the device, e.g., so that the function of the patient's liver can be assessed.

Charcoal Hemoperfusion

One example of the conventional systems is a portable hepatic-assist method and apparatus disclosed in U.S. Pat. No. 4,209,392. This system employs a hemofiltration membrane (plasma separator) having a plurality of microporous membranes with an average pore diameter of approximately 5 to 50 microns, and a sterilizable disposable sorbent cartridge for adsorption of hepatic toxins. Blood from the patient is passed through the plasma separator, and the fluid portion of the arterial blood containing substantially all hepatic toxins is removed from the blood. Thereafter, the hemofiltrate is passed through the activated charcoal-type sorbents cartridge, and the detoxified hemofiltrate is filtered through a fine submicron particulate filter via a valve regulator to remove any bacteria, sorbents, and pyrogens, and is passed to a detoxified hemofiltrate reservoir. The detoxified hemofiltrate is preferably heated, checked for proper pH and electrolyte levels, and then either returned to the patient's blood or recirculated in the closed loop hemofiltrate circuit.

This conventional device, while providing a closed loop system, also has several drawbacks. For example, a plasma separator is required, and the method is directed to operating under the concept of plasma separation. This is a problem because plasma separation is not typically performed continuously for more than 4-6 hours. In addition, plasma lacks the oxygen carrying capacity of whole blood. Metabolically-active cells will become anoxic under these circumstances. This problem will be further exacerbated by the use of a closed hemofiltration loop which will allow further oxygen depletion of the plasma. Additionally, the hemofiltrate is mixed with a physiological salt solution and is stored temporarily in a reservoir which is needed to replenish the blood to the patient. Furthermore, the pore size of the hemofiltrate membrane is fairly large, and is on the order of 0.1 to 0.5 microns. This type of fiber permits the passage of immunoglobulins which are potentially harmful to the living cells in the extracapillary space. Finally, the system is not able to support a metabolically-active device once blood flow is diverted from the device.

Plasmapheresis

Another conventional type of device is a plasmapheresis machine which can also be utilized with a cartridge. Plasmapheresis involves the separation of blood into a plasma fraction (ultrafiltrate) and a cellular component fraction (red cells, white cells, and platelets) which make up approximately 45% of the blood volume. The treatment is performed in patients who have toxic substances circulating in the plasma fraction of their blood. The ultrafiltrate is drawn into the extracapillary space of a cartridge at a rate of approximately 50-100 ml/minute, and the cellular components are returned to the patient with a replacement fluid. The plasmapheresis system has several shortcomings which preclude its use as a support system for cellular-based therapies. First, plasmapheresis is designed for fluid removal, but not for return of the ultrafiltrate to the patient. Second, an in-line filter is not part of the system since cellular elements in the ultrafiltrate pose no threat. Third, it is not designed to allow sampling of the ultrafiltrate. Fourth, there is no need to assure a continuous positive pressure gradient from the ICS to the ECS since there is no risk of cells washing back into the blood stream. Fifth, the system cannot attain flow rates sufficient to sustain a large mass of living cells. Sixth, the system cannot support a metabolically-active device once blood flow is diverted from the device.

Ultrafiltration

A closely related method to plasmapheresis is ultrafiltration, as mentioned above, which can be used on a continuous basis for, or in combination with, dialysis. Ultrafiltration relates to filtering out the macromolecular substances having molecular weights higher than approximately 10,000, and generally at least 40,000-50,000, and which includes blood cells and the like from the remaining ultrafiltered aqueous portion of the blood. Ultrafiltration differs from plasmapheresis in that the blood is not separated into plasma and cellular components, but instead into macromolecular fractions which include the cellular components and portions of the plasma, and a low molecular fraction which must be removed as waste. This process requires that the flow rates of the ultrafiltrate be carefully controlled. This system is not suited to the purpose of the organ support system for the same reasons mentioned above regarding plasmapheresis.

As discussed above, the foregoing conventional systems and methods have several drawbacks which make them unsuitable for an organ support system.

SUMMARY OF THE INVENTION

In view of the foregoing problems of the conventional methods, an object of the present invention is to provide a new and improved support system and method for sustaining a bodily organ such as a liver having high flow rates and which can be monitored for patient safety.

A second object of the present invention is to provide a means of implementing treatment with an organ support system which maintains viability of cells in a cartridge during treatment.

A third object is to provide a system in which a pressure gradient from the ICS to the ECS is maintained continuously during therapy.

A fourth object is to provide a support system which is designed such that a dialysate is not required to detoxify blood and the like.

A fifth object is to provide a closed loop system in which there is no appreciable shifting in the patient's balance (other than the fluid recirculated in the extra-corporeal circuit) and which allows continuous and accurate measurement and control of the volume of fluids removed from the patient.

A sixth object of the invention is to provide an organ support system which can be operated continuously.

A seventh object is to provide an apparatus in which blood returned to the patient is sterile and pyrogen-free.

An eighth object is to provide an apparatus in which an ultrafiltrate is returned to the patent's blood stream in a sterile and pyrogen-free manner.

A ninth object is to provide an organ support system which is regulated in such a manner as to assure that treatment is automatically discontinued in the event that an untoward event occurs.

A tenth object is to provide an organ support system which does not require continuous human monitoring other than to respond to an alarm.

An eleventh object is to provide an organ support system in which oxygenation of a biologically active device can be monitored.

A twelfth object is to provide an organ support system which is capable of supporting a metabolically-active device (such as an artificial organ) during varying periods of disconnection from the patient in order to allow such activities as testing of the patient's own organ function.

According to the present invention, the above objects are accomplished by an organ assist and support method and apparatus having a closed loop system and designed for use with an organ (e.g., liver) assist device including cells placed in a hollow fiber or similar cartridge in which blood flows from the patient through the cartridge and returns to the patient. A small fraction of the blood flow is continuously ultrafiltered and passed through the cell space, is checked to determine integrity of the fibers of the cartridge, is filtered to remove any cells potentially harmful to the patient, and is then returned to the blood stream. This dual flow path with safety checks, return of fluid from the ECS to the patient's blood stream, and a mechanism for preventing cells from returning to the patient are some of the unique aspects of the invention.

More specifically, the apparatus includes an organ assist device, an access ("arterial") line having one end coupled to the patient and a second end coupled to an input of the cartridge to return the treated fluid thereto, a cell line having one end coupled to the cartridge and a second end coupled to the second line, the cell line including a mechanism for detecting leaks in the cartridge and preventing loose cells from returning to the patient's blood, and a control system for controlling operations of the organ support system.

The method for treating blood or body fluids of a patient according to the invention is adapted for use with a fluid modifying (e.g., detoxifying) device, and includes: removing the fluid from the patient; passing the fluid through a fluid modifying device adapted to the condition being treated, the fluid modifying device having a semi-permeable membrane and a molecular weight cutoff of between 10,000 and 250,000 and preferably 70,000; withdrawing a flow of fluid from the extra-capillary space of the fluid modifying device to determine whether the fluid from the extra-capillary space has been modified; and returning the fluid having been modified to the patient, wherein the organ assist device is capable of filtering proteins having a molecular weight of between 10,000 and 250,000, and preferably between 60,000 and 80,000, the fluid being passed through the device and being modified by both the diffusion of molecules across the semi-permeable membrane, and by the passage of ultrafiltrate across the membranes into the ECS. The ultrafiltrate which is returned to the patient is supplemented with synthetic products of the cells in the ECS.

The organ support system is designed to be operated in an intensive care setting, and is an extracorporeal system in which the patient's blood is accessed and delivered to the therapeutic device (e.g., the artificial liver cartridge) through plastic tubing similar to that used in artificial kidney treatment, therapeutic plasma exchange, open heart surgery, standard intravenous methods, etc. Additionally, the pressure of the tubing and the blood flow therethrough can be monitored at various points in the extracorporeal circuit. These pressure monitors are similar to those used in hemodialysis and therapeutic plasma exchange systems.

The control system provides flow control through pumps, monitors the pressures, and monitors the patient return (venous) line to ensure that air is not pumped to the patient. The control system also includes the operator interface where the flow rates and alarm levels are set and where the measured pressures are displayed.

Since the apparatus does not utilize a dialysate, none of the issues attendant thereto, particularly preparation, quality monitoring and flow control, is of concern.

Additionally, since the system has a closed loop configuration in which the patient has first and second lines connected thereto with the organ assist device and cell line therebetween, there is no appreciable shifting of patient fluid balance, and the control of patient fluid balance is not an issue. As mentioned above, in conventional hemodialysis machines, one of the crucial treatment issues is the control of the removal of excess fluid from the patient. A considerable portion of the conventional hemodialysis hardware and software is devoted to monitoring, controlling and assuring appropriate fluid removal. The method and apparatus of the invention does not involve any appreciable shifting of the patient's fluid balance. Consequently, these hemodialysis issues, which pertain to fluid balance, are not of concern.

Further, the apparatus may be operated nearly continuously and without human supervision, for several days in an intensive care unit or other specialized setting.

DETAILED DESCRIPTION OF THE PREFERRED EMBODIMENT

Figure 1:
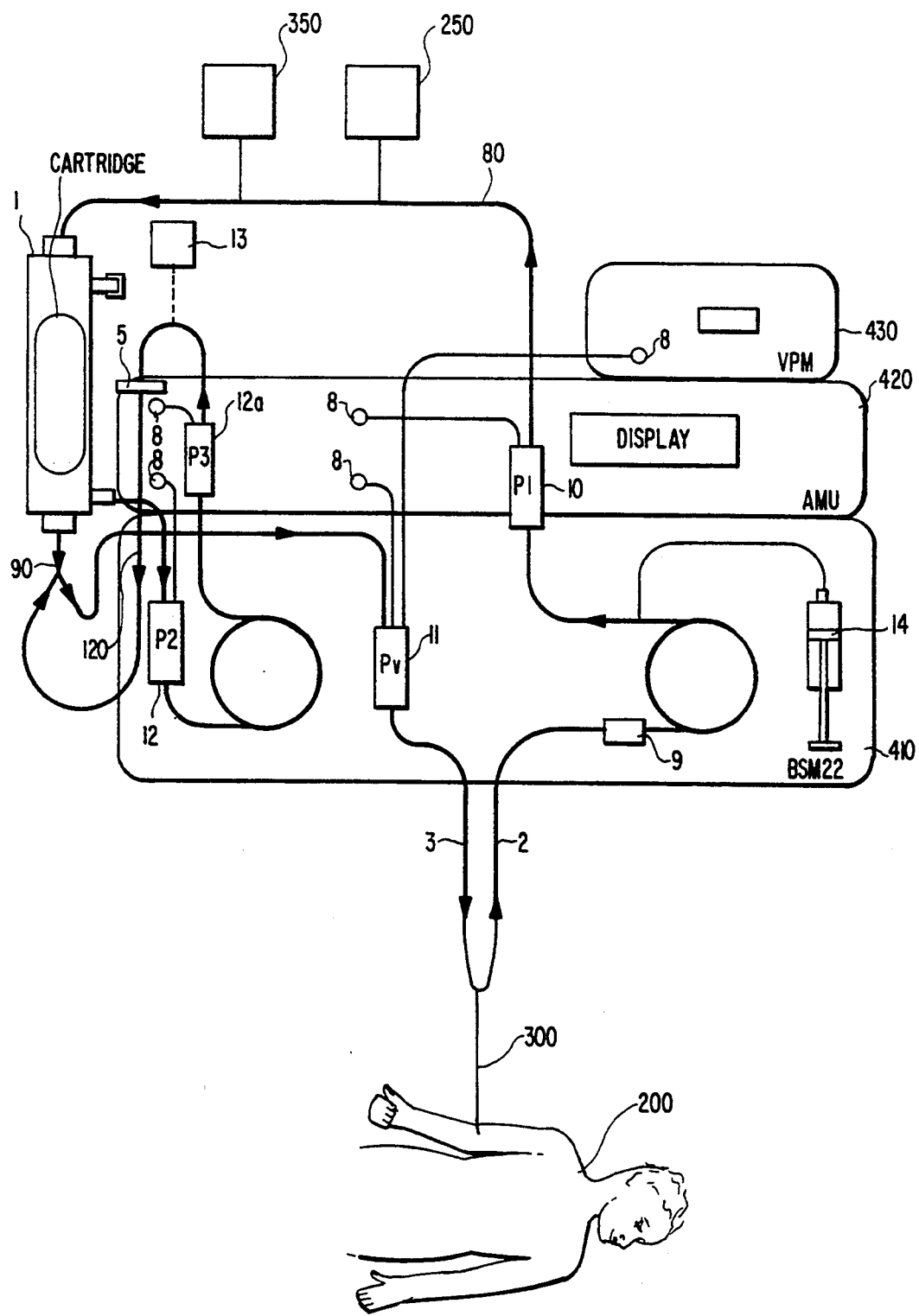
FIG. 1 is a schematic view of tubing connections for an organ assist device of the organ support system according to the invention.

A preferred embodiment of the invention is described hereinbelow with reference to FIGS. 1-5. An external organ (e.g., liver) assist device 1 for modifying (e.g., regulating, detoxifying, etc.) the bodily fluid (e.g., blood) of a patient 200 having either two individual venous catheters (unreferenced) or a double lumen venous catheter 300 or the like connected thereto, has an input coupled to an "arterial" line 2 leading from the patient 200 to receive the blood from the patient. An output of the organ assist device 1 is connected to a "venous" line 3 returning the modified body fluid to the patient. "Arterial" and "venous" are used to designate access and return lines. The use of a double lumen catheter indicates that access and return are to the same blood vessel. This nomenclature is commonly used in the description of extracorporeal circuits, and is used for convenience. The venous vessels typically used with the double lumen catheter are the femoral, subclavian, or internal jugular. It is noted that the use and operation of the double lumen catheter is well known. Further, it is noted that the organ assist device has been employed previously without any external elements used to pump blood through the device. Specifically, the organ assist device has been employed with a 68-year-old patient in which the patient's arterial flow was used to pump the blood through the device.

An example of the external organ assist device which is preferably used with the system is a cell line commercially available from Baylor College of Medicine and designated as C3A. The cell line is designed to be inserted into a hollow fiber cartridge to form the external organ assist device cartridge. As discussed below, the organ assist device in this embodiment is an extracorporeal liver assist device (LAD). As used herein, "fiber" preferably means a cylindrical fiber made of a semipermeable material such as cellulose acetate and having an internal diameter of approximately $200\mu$ and a wall thickness of approximately $30\mu$. However, the fiber may have other shapes and other internal diameters and wall thicknesses. The characteristics of the hollow fiber cartridge include an outer shell which contains a plurality of fibers, and which provides independent access to the ECS and the ICS.

Looking at the liver assist cartridge and the cell line used therein in greater detail, the cell lines are liver cell lines derived from a hepatoblastoma that retain most of the characteristics of the human hepatocyte. As used herein, "hepatoblastoma" is a liver tumor of unknown etiology, but is presumed to be the result of inactivation of a tumor suppressor gene. "Hepatocyte" means a normal human liver cell which performs the metabolic functions which are typical of the normal human liver. The cell lines are able to mimic the liver both qualitatively and quantitatively. The cell lines express near normal levels of several central metabolic pathways, including glycolysis, gluconeogenesis, glycogenesis and ureogenesis. Additionally, these cells synthesize near normal levels of albumin and other serum proteins, contain high levels of liver specific transcription factors, and exhibit the structures and polarity characteristic of the human hepatocyte.

The cell lines are derived from a known hepatoblastoma cell line, HepG2. By "derived" it is intended that the cell line is obtained or cloned from HepG2 by a defined selection method. The HepG2 line is a human hepatoblastoma cell line which exhibits certain characteristics of normal human hepatocytes. The cell line is disclosed in U.S. Pat. No. 4,393,133 and is available from the American Type Culture Collection (ATCC), Rockville, Md., as ATCC No. HB8065. Characteristics of the cell line have been discussed in publications including Darlington et al., *In Vitro Cellular and Developmental Biology* 23;349-354; Kelly et al. *In Vitro Cellular and Developmental Biology* 25:217-222; Darlington, G. J., *Meth. Enzymol.* 151:19-38 (1987); Thrift, R. N., et al., *J. Lit). Res.* 27:236-250 (1986). Unlike most other human liver lines, HepG2 does not carry any human hepatitis B virus (HBV) genetic sequences. Thus, the cell lines of the invention, clonally derived from HepG2, do not carry any HBV genetic sequences.

The cell lines may be obtained from the HepG2 line by selecting for cells which show: (1) strong contact inhibition; (2) high expression of albumin; (generally at least about 20 $\mu$g/mg total cell protein/24 hr, more generally at least about 25 $\mu$g/ml total cell protein/24 hr); and (3) high albumin to alphafetoprotein ratio at confluence (generally a ratio of at least about 15, more generally at least about 25). This is discussed in greater detail in U.S. Pat. application Ser. No. 07/524,075 and PCT WO 91/18087, both incorporated herein by reference. A preferred cell line is C3A, which is described more fully below. This cell line has been deposited at the American Type Culture Collection under ATCC No. CRL-10741.

The selected cell lines synthesize levels of human albumin and other serum proteins that are similar to levels produced by normal human hepatocytes and demonstrate regulation of gene expression as is predicted for developing or regenerating normal hepatocytes. As indicated, such cell lines are cloned by selection for high albumin production and a high albumin to alphafetoprotein (AFP) ratio when the cells reach confluence. The term confluence refers to the cell density in culture when the cells begin to contact one another and cover most or all of the available growth surface.

In the preconfluent phase of growth, selected cells behave like a regenerating liver. They have a rapid doubling time (about 24 hr) and express a number of fetal proteins, including AFP, aldolase A/C and pyruvate kinase K. Upon reaching confluence, the cells assume an adult phenotype wherein cell division slows dramatically (doubling time >200 hr) and expression of fetal proteins is extinguished. Cells expressing an adult phenotype become predominant, as evidenced by production of albumin, aldolase B, and pyruvate kinase L, and development of histologic features of a normal liver.

The cell lines of the invention have several distinct advantages over hepatoma cell lines known in the prior art. They are extremely well differentiated. Consequently, they constitutively express liver-specific biological activities at a level sufficient to support a subject in hepatic failure or insufficiency for either short or long periods.

The term "constitutively" refers to the fact that these cells normally express liver-specific biological activities without any need for particular forms of induction. Once these cells reach confluence, when they grow to fill the available surface, they maintain normal liver-specific biological activities.

The term "liver-specific biological activity" as used herein refers to a number of physiological/biochemical reactions which take place specifically in hepatocytes, as well as in the cells of the present invention. Also intended by this term are the proteins, protein complexes, lipids and lower molecular weight products which these cells synthesize and secrete.

Hepatocytes perform multiple finely-tuned functions which are critical to homeostasis. Of the variety of cell types in the mammalian body, only hepatocytes combine pathways for synthesis and breakdown of carbohydrates, lipids, amino acids, proteins, nucleic acids and co-enzymes simultaneously to accomplish a unique biological task. The key "liver-specific" biological functions include: (1) gluconeogenesis; (2) glycogen synthesis, storage and breakdown; (3) synthesis of serum proteins including albumin, hemopexin, ceruloplasmin, the blood clotting factors (including Factors V, VII, IX, X, prothrombin and fibrinogen), $\alpha$1-antitrypsin, antithrombin III and AFP; (4) conjugation of bile acids; (5) conversion of heme to bile pigments; (6) lipoprotein synthesis; (7) vitamin storage and metabolism; (8) cholesterol synthesis; (9) ammonia metabolism, including urea synthesis and glutamine synthesis; (10) amino acid metabolism, including metabolic conversion and re-utilization of aromatic amino acids; and (11) detoxification and drug metabolism.

The cells of the invention are believed capable of performing all classes of the "liver-specific" biological functions. All functions have been tested except for classes 4 and 5. Exemplary functions include the ability to perform ammonia metabolism, amino acid metabolism, detoxification, and protein production, especially of coagulation factors. These four groups of liver-specific biological functions are of particular importance where the cells are to be used in a liver assist device (LAD).

For support of subjects in the form of relatively short term LADs, such as patients with fulminant hepatic failure (FHF), patients awaiting liver transplantation, or patients with nonfunctioning liver grafts, the four groups of liver-specific biological functions noted above are believed to be of central importance. However, notwithstanding the above, there may be others of equal or greater importance. The other functional deficits can be provided by other means (such as by provision of glucose and monitoring of glucose levels) or do not require acute attention (for example, conjugation of bile acids or bile pigment production, or drug metabolic activity).

The levels of liver-specific biological activity "sufficient to support" a subject suffering from hepatic failure or insufficiency are those which will result in normal or near normal levels of serum proteins, coagulation factors, amino acids, and other metabolites produced in or metabolized by the liver. These improvements may be measured biochemically or by an improvement in patient's clinical status. These various molecules, metabolic and clinical parameters and products and the physiological as well as pathological ranges of their concentrations or levels are well known in the art and are set. forth, for example, in Zakim & Boyer, *Hepatology; A Textbook of Liver Disease*, W. B. Saunders Company; Harcourt, Brace, Jovanovich, Inc., Philadelphia, London, Toronto, Montreal, Sydney, Tokyo, (1990), which is hereby incorporated by reference.

Once a particular cell line has been selected based upon the initial criteria of strong contact inhibition, high expression of albumin, and a high albumin/alphafetoprotein ratio at confluence, the cell line can then be tested for the performance of liver-specific biological functions. Thus, tests as described below can be performed to examine the metabolic functions of the cells, particularly in an environment in which the cells can be used as a liver assist device. Metabolic functions tested include oxygen dependence, glucose and urea synthesis, bilirubin uptake and conjugation, and clotting factor biosynthesis.

The liver is an extremely aerobic organ and accounts for 20% of the body's oxygen consumption. Like the liver in vivo, it is noted that the cultures of the invention require oxygen for high-level liver-specific function (see U.S. patent application Ser. No. 07/524,075). Provision of adequate oxygenation may stimulate both growth and differentiated function in selected cells. The effect of oxygen on selected cell lines may be tested in several ways, including the following:

(1) The growth rate of the cells in continuously perfused cell culture may be examined in increasing concentrations of dissolved oxygen (4–20%). Growth rate can be examined in a standard medium containing high concentrations of glucose and in glucose-free medium containing lactate and amino acids as the only carbon source. As gluconeogenesis is exceedingly oxygen-sensitive, one would expect cell growth to be more dramatically affected in the glucose-free medium as compared to cells in the presence of glucose.

(2) Indicators of metabolic activity may also be measured in the cells at different concentrations of oxygen. Such metabolic activities include total oxygen consumption, energy charge, redox state, and the ratio of glucose consumption to oxygen consumption.

The logical extension of these experiments is the application of the patient treatment. Since the cell function is associated with an adequate oxygen supply, the continuous or intermittent monitoring of the blood flowing through the device may be performed. Accordingly, a device 350, as illustrated in FIG. 1, for monitoring oxygen tension of the blood flowing through the extracorporeal blood line may be employed. For example, a commercially available $O_2$ sensor may be used. Similarly, other parameters such as temperature or the like may be monitored as desired. The monitoring device may be coupled to the auxiliary monitoring unit 420 to alert the operator of unsatisfactory levels. It is envisioned that external monitoring devices could be developed for non-invasive detection. While the monitoring device 350 is shown coupled to the arterial line 80 in FIG. 1, the monitoring device(s) may be employed at any position in/on the extracorporeal blood line.

Glucose and urea synthesis are the primary means of removing excess amino acids and ammonia from the blood. Amino acid catabolism results in the liberation of carbons which are shunted into the citric acid cycle and thence to glucose. The nitrogen released during this process is used in the synthesis of urea. Therefore, a selected cell line must synthesize both glucose and urea. Methods for measurement of glucose and urea are known in the art, for example see Kershcer et al., in *Methods of Enzymatic Analysis*, H. U. Bergmyer, ed., 3rd ed., Verlag Chemie, Weinheim, Vol. VII, pp. 59-67 (1983).

Elevated serum bilirubin is a highly visible indicator of liver disease. While not generally toxic in adults, high circulating levels of unconjugated bilirubin may produce brain damage and even death in neonates. This condition is known as kernicterus because of the typical yellow appearance of the brain stem nuclei at postmortem examinations. The ability of the selected cell lines to metabolize bilirubin may be examined, for example, using oxygenated monolayer cultures. For this test, serum from patients with hyperbilirubinemia can be incubated with oxygenated cells to determine whether the cells are able to conjugate the bilirubin. Direct binding studies may be carried out using [$^3$H]-bilirubin in the presence and absence of unlabeled competitor in order to determine $V_{max}$ and $K_m$.

The cell lines are also tested for clotting factor biosynthesis. Many of the clotting factors are synthesized by the liver, and the development of a severe coagulopathy is an ominous sign in FHF. Although all of the vitamin K dependent group is affected, antithrombin III (AT III) has been identified as the most significant deficiency. The cell lines are tested for the ability to synthesize fibrinogen, prothrombin, factors VII, and X, and AT III. The levels of production of these factors may be quantitated using commercially available antibodies.

The properties of the cell lines make them particularly useful in liver assist devices (LAD). For the most part, the cells may be used in any device which provides a means for culturing the cells, as well as a means for separating the cells from blood which will be passed through the device. Membranes or capillaries are available in the literature for use which allow for the crossover of toxic solutes from the blood to the cells as well as the diffusion of vital metabolites provided by the cells across the membrane into the blood. The permiselective or semipermeable membrane additionally provides a mechanical barrier against the immune system. For the most part, a membrane or capillary is used which features a molecular weight cutoff from about 10,000 up to about 250,000, and generally about 60,000 to 80,000 (preferably 70,000).

Generally, the cells are grown in the liver assist device. After growth of the cells, the subject's blood is passed through the device, and dissolved molecular species (e.g., bilirubin) diffuse through the membrane and are taken up and metabolized by the cells. For the most part, the devices are based primarily on extracorporeal blood processing. Generally, the devices are designed to house the cells in a blood-perfused device attached to the blood stream. Typically, the device is attached to the blood stream by vein, as discussed below in more detail.

Several designs of liver assist devices are known in the literature. For example, devices have been described by Viles et al., U.S. Pat. Nos. 4,675,002 and 4,853,324; Jauregui, Great Britain Pat. No. 2,221,857A; Wolf et al., *International J. of Artificial Organs* 2:97-103 (1979); Wolf et al., *International J. of Artificial Organs* 1:45-51 (1978); and Ehrlich et al., *In Vitro* 14:443-450 (1978), which disclosures are herein incorporated by reference. Preferred devices include the hollow fiber cartridge and similar perfusion devices.

Bioreactors, such as hollow fiber bioreactors, may be utilized as liver assist devices. Such bioreactors, such as the Anchornet series, are known in the literature and are available commercially. See, for example, Heifetz et al., *BioTechniques* 7:192-199 (1989); and Donofrio, D. M., *Amer. Biotech. Lab.* September 1989, Publication #940, which disclosures are herein incorporated by reference. Commercially available dialysis cartridges such as Althin CD Medical, Inc. (of Miami Lakes, Fla.) Altraflux may also be used.

The cells of the invention, when grown in a hollow fiber cartridge or similar perfusion device with capacities for high numbers of cells, can function as a perfused liver, allowing accurate assessment of human liver metabolism and replacement of liver-specific biological activities. Therefore, a perfusion device containing a culture of the disclosed cells is capable of functioning as a liver assist device. In the preferred embodiment of this invention, the LAD is extracorporeal, referring to its connection to the circulation outside the body. An extracorporeal LAD (or ELAD) is particularly useful for providing temporary liver support for subjects suffering from FHF. It is envisioned that the LAD could also be implanted in the body, that is, "intracorporeal". This embodiment may be advantageous as a longer term LAD.

For use in a liver assist device, the cells are generally grown on the membrane or porous support which may be formed of cellulose acetate. For the most part, the cells attach to the support upon growth. However, it is recognized that linkage materials may be provided to attach the cells to a support. Suitable linkage materials are known in the art. See, for example, Jauregui, Great Britain Patent No. 2,221,857A.

Hollow fiber cartridges are two-chamber units which reproduce the three-dimensional characteristics of normal organs (Knazek, R. H., *Feder. Proc.* 33:1978-1981 (1974); Ku, K. et al., *Biotechnol. Bioeng.* 23:79-95 (1983)), which references are hereby incorporated by reference. Culture or growth medium is circulated through the capillary space and cells are grown in the extracapillary space (Tharakan, J. P. et al., *Biotechnol. Bioeng.* 28:1605-1611 (1986). Such hollow fiber culture systems have been disclosed as useful for culture of hybridoma cells lines for the production of monoclonal antibodies (Altshulter, G. L. et al., *Biotechnol. Bioeng.* 28:646-658 (1986); Heifetz, H. H. et al., (*BioTechniques*

7:192–199 (1989); Donofrio, D. M., *Amer. Biotech. Lab.*, September 1989, Publication #940)). Further, a number of other cell types, including the liver cell lines PLC/PRF 5 and Reuber hepatoma, (McAleer, W. J. et al. *J. Virol. Meth.* 7:263–271 (1983); Wolf, C. F. W. (1982)) and pancreatic islet cells (Araki, Y. et al. *Diabetes* 34:850–854 (1985)) have been cultured in this manner. Cells could conceivably be grown inside the fibers.

Once a device has been chosen for use as a liver assist device, it is provided with the appropriate medium and an inoculation of cells. Generally, cells are grown in a complex media, for example, in a 3/1 mixture of Eagle's MEM with Earle's salts (Gibco) and Waymouth's MAB 87/3 (Gibco) 30 containing 10% defined/supplemented calf serum (Hyclone). The devices are then maintained at 37 degrees C. with constant recirculation of medium and constant inflow of fresh medium. Each cartridge growth circuit includes a membrane oxygenator which maintains oxygen saturation of the medium. For use with a hollow fiber cartridge, using a ~2 $m^2$ hollow cartridge, the cartridge is provided with 150 ml/min of recirculated medium with a constant inflow of about 0.3–1.0 ml/min. A 2 $m^2$ cartridge is generally inoculated with about $1 \times 10^9$ cells.

The function of the cells in the device can now be tested for the capability of the device to function as a liver assist device. This includes measurements of essential liver biological functions as discussed above.

For the most part, it will not be necessary to add additional oxygen to the membrane oxygenator. However, the oxygen tension in the cultures can be determined and additional oxygen added if necessary.

In order to vary the oxygen tension in cultures of the selected cell lines to determine the optimum oxygen level, cells can be grown in a continuous perfusion apparatus. The apparatus will consist of a recirculation pump, medium bottles, and a lid that fits on a standard 6-well culture dish. The medium is continually recycled over the surface of the cells and back into the medium container where it can be gassed. Medium will be gassed with preparations containing between 4% and 20% oxygen, 5% $CO_2$ and the remainder nitrogen. In this way, the cells can be maintained in the appropriate atmosphere such that the effect of the gas mixture can be determined. Growth rate may be determined by monitoring total cell protein per well.

ATP, ADP and AMP will be measured as described by Lundin et al., *Meth. Enzymol.* 133:27–41 (1986), using firefly luciferase. The ratio of NAD/NADH can be calculated from the ratio of lactate to pyruvate across lactate dehydrogenase and from the ratio of malate to oxaloacetate across malate dehydrogenase. The concentrations of these metabolites can be determined as taught by the methods set forth in *Methods of Enzymatic Analysis*, H. U. Bergmyer, ed., 3rd ed., Verlag Chemie, Weinheim, Vol. VI, pp. 570–588. The ratio of NADP/NADPH may be calculated from the ratio of isocitrate to alpha-ketoglutarate across isocitrate dehydrogenase and from the ratio of malate to pyruvate across malic enzyme. The determination of these metabolites is also set forth in *Methods of Enzymatic Analysis*. Energy change may be calculated from the equation (ATP+0.5 ADP)/(ATP+ADP+5 AMP). Besides looking at the oxygen dependence of the liver assist device, the devices will also be characterized with respect to their ability to simulate an isolated, perfused human liver. This includes testing the device for glucose and urea synthesis, bilirubin uptake and conjugation, and clotting factor biosynthesis as described above. Urea may be quantitated using a coupled glutamate dehydrogenase/urease assay. Glucose may be determined using a dye-coupled glucose oxidase assay. The assays for urea and glucose determination are found in *Methods of Enzymatic Analysis*. As discussed earlier, the various vitamin K dependent clotting factors, prothrombin, factors VII, IX and X, as well as antithrombin III, can be determined using a solid phase radioimmunoassay as described by Kelly et al., *In Vitro Cell Dev. Biol.* 25:217–222 (1987). Antibodies for the immunoassay may be obtained from DAKO, Inc.

In a preferred LAD embodiment, the cell line C3A (as mentioned above, commercially available from Baylor College of Medicine) is provided in a hollow fiber cartridge (as also mentioned above, commercially available from Althin CD Medical, Inc.) for use as a liver assist device. The device comprises hollow fiber capillaries contained within a plastic housing. A seal around the ends of the fibers provides two spaces (an ICS and an ECS). Media are circulated through the ICS and cells are grown in the ECS.

For the growth of cells, cells are seeded into the extracapillary space and supplied a constant inflow of fresh medium. 2 $m^2$ cartridges are inoculated with an effective number of cells, usually about $1 \times 10^9$ cells, and grown to confluence, usually about 28 days.

The medium supplied is generally a complex medium, as mentioned above, usually a 3/1 mixture of Eagle's MEM and Earle's salts containing 10% defined/supplemented calf serum. This provides nutrients for cell growth. Thus, the cells grow on the outer surface of the capillaries. The hollow fiber cartridge containing the confluent cells is capable of functioning as a liver assist device for supporting a subject suffering from hepatic failure or insufficiency.

The cell lines may also find use as bioartificial livers or liver supports. In this manner, the cells are encapsulated or grown in hollow fiber capillary membranes for use as bioartificial organ. The cells are encapsulated in biomaterials such as alginate-polylysine membranes, as taught by Cai et al., *Artificial Organs* 12:388–393; Sun et al., *Trans. Am. Soc. Artif. Intern. Organs* Vol. XXXII:39–41 (1986); O'Shea et al., *Biochimica Biophysics Acta* 804,:133–136 (1984); Sun et al., *J. Controlled Release* 2:137–141 (1985); and U.S. Pat. No. 4,391,909. The encapsulated cells and vehicle capsules are then injected intraperitoneally into a subject (along with other insertion devices such as straws, bags, etc.).

The novel cell lines are useful for studies of human liver metabolism as well as the study of liver specific gene regulation. The cell line is originally derived from a human hepatoblastoma, not from a human hepatoma as is the usual case with human liver cell lines. The cell lines are useful for studying all liver functions, including metabolic functions and liver specific gene expression. They also provide a useful in vitro liver model.

The cells and cell lines may also be used for studying the metabolism and/or toxicology of drugs or other pharmacological compositions. The cells, grown on a membrane or liver assist device, serve as a prototype artificial liver. Thus, the clinical effects and metabolic byproducts of various drugs or compounds can be assessed in an in vitro model. The cells grown in liver assist devices are also useful for the production of serum proteins. As indicated the cells exhibit liver specific biological activity and synthesize serum proteins, isoenzymes, clotting factors and the like. Accordingly the cells can be utilized as an in vitro factory for these proteins. In this manner, the supernatant fluid is recovered from the cell culture and the plasma proteins isolated and purified. For convenience, the cells may be grown on a semipermeable membrane which allows for diffusion of serum proteins across the membrane where they are isolated and purified for further use.

As the cells are capable of functioning as a liver model, they are also useful for studying viral hepatitis. This particularly true as the cell lines are not transformed by hepatitis B virus (HBV) and do not carry any HBV sequences.

The liver cells disclosed in the present invention have advantages over other systems known in the art, such as the isolated perfused rat liver (IPRL). The cultures are permanent. That is, they have an indefinite life-span, thereby allowing the effects of long-term exposure to be studied in an experimentally rigorous situation. Monolayer cultures of the permanent cell lines are typically maintained for several months and a liver assist device prepared according to the methods of the invention functions normally over at least an indefinite period, generally eight to twelve weeks, as determined by albumin production and glucose utilization. LADs have been maintained for 6–8 months by the present inventors. Use of the culture methods of the invention reduces the need for the regular sacrifice of animals required for liver perfusion, which comports with current U.S. government goals (NIH Guide for Grants and Contracts, supra). Finally, the cartridges containing cultured cells of the invention reflect human metabolism more closely than the isolated perfused livers from other species.

The inventive system, particularly the use of a hollow fiber-based system, offers several advantages as liver assist devices. Cartridges support the growth of very high density cultures. Based on the extracapillary volume, 200 g of cells can be grown in a2 $m^2$. The unit is capable of achieving sufficient cell mass to provide liver support to a subject suffering from liver failure.

Cartridge-grown cells are polarized and their growth approximates normal liver structure. The cells receive nutrients from the ICS and secrete complex metabolic products into the ECS and back to the ICS. The ECS can be perfused to prevent accumulation of toxic products although no toxic product has been identified at the present time and perfusion of the ECS has not been necessary. The continual flow of media and an in-line oxygenator may be employed as discussed below to provide a more constant supply of oxygen and energy. Thus, the organ (e.g., liver) assist device is inserted in-line with the patient's blood flow to modify (e.g., metabolically regulate, filter, detoxify, etc.) the blood.

Figure 5:
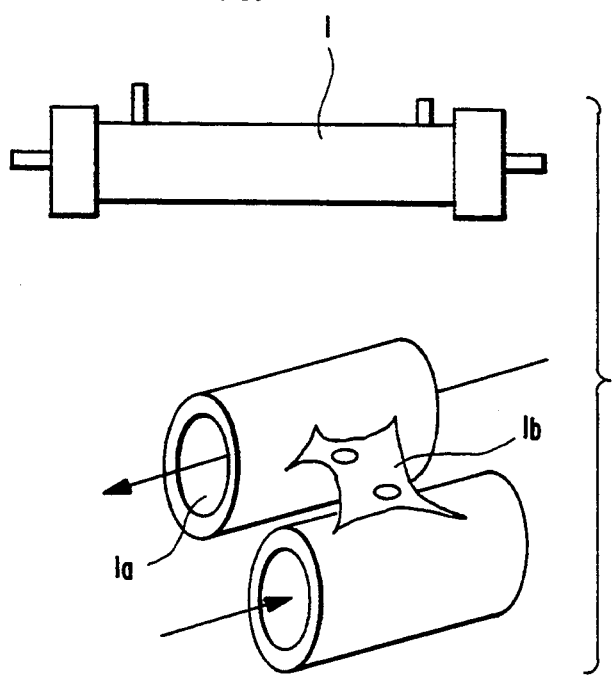
FIG. 5 is a schematic view of an organ assist device used in the invention.

FIG. 5 shows an example of a cross-section of two fibers illustrating their ICS 1a and their ECS 1b with cells growing on their outer surfaces. Thus, media are circulated through the ICS and cells are grown in the ECS of the cartridge.

To monitor the integrity of the organ assist device 1 which has been placed in a hollow fiber cartridge, a recirculation tubing set, as shown in FIGS. 1, 2b, 3, 6 and 10, has a first end connected to the device 1, and a small volume of fluid its withdrawn from the extracapillary space of the device 1. The fluid in the extracapillary space can be checked for hemoglobin or the like which would indicate a leak in one or more of the hollow fibers of the cartridge. To prevent any cells from returning to the patient, a filter mechanism or the like may be installed on the fluid line from the extracapillary space. Any of a variety of filters may be employed to include a 0.45 $\mu$m filter. Additional filters may be placed in the extra-capillary space fluid line for additional safety. For example, a tandem filter set may be employed. The tandem filters may be commercially available from Arbor Technologies or Gelman Corporation, both of Ann Arbor, Mich. The recirculation tubing set has a second end connected to the outlet tubing of the organ assist device 1.

Figure 4:
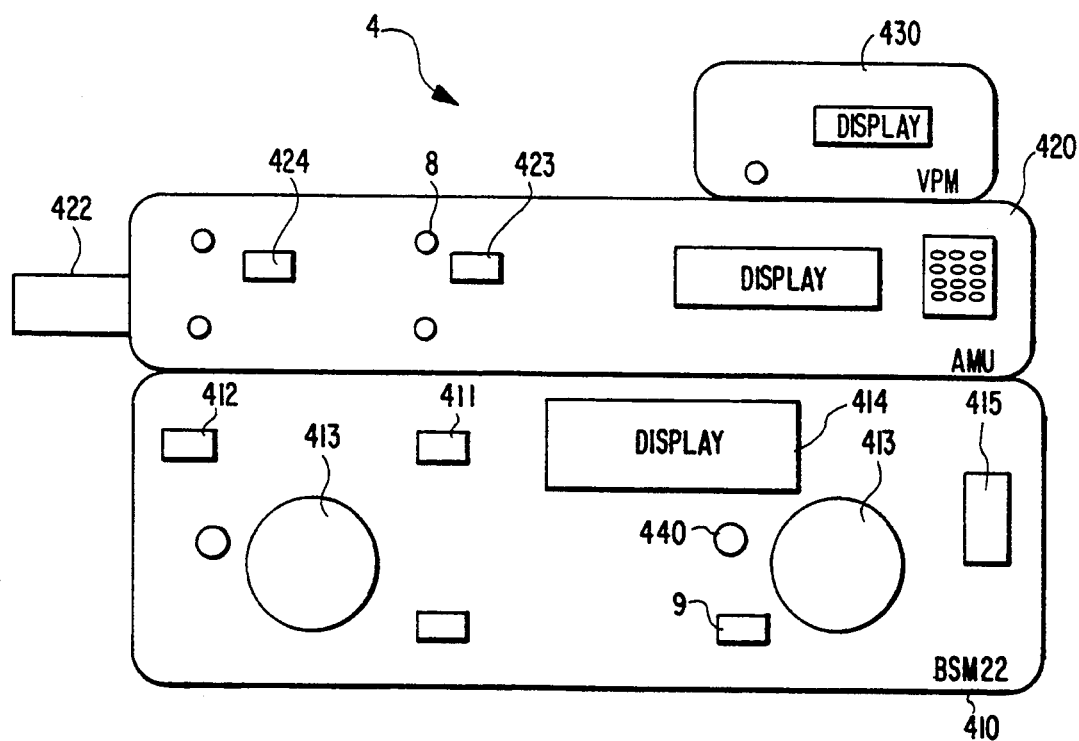
FIG. 4 is a front view of the control system of the invention.

As shown in FIGS. 1 and 4, a control system 4 including three modules controls the overall system operation. The control system may include the three modules in a single integrated, or as separate modules, as shown in FIGS. 1 and 4. One of the three modules comprise a dual pump system which is the primary control module 410. Module 410 is commercially available (e.g., a BSM-22 Dual Pump Blood Safety Module commercially available from CGH, Inc. of Lakewood, Colo.).

Another module of the control system is an auxiliary monitoring unit (AMU) 420 which is designed to monitor pressures, accept alarm settings from the operator by a keypad or the like, and, in turn, notify the operator if certain alarm limits are reached. The primary control module 410 and the AMU 420 are mounted together so that relative motion therebetween is prevented. The primary control module 410 also may have one or more alarm units associated therewith. In certain cases, as discussed below, the AMU can initiate a system shutdown alarm.

The third module of the control system is a Venous Pressure Monitor (VPM) 430 which monitors the pressure in the venous return to the patient in an extracorporeal circuit during treatment. The VPM, also commercially available from CGH, Inc., may include two types of alarms. A first type of alarm has a limits window such that the alarm is triggered when the pressure value is 40 mmHg or lower or 70 mmHg or greater than the selected value. A second alarm is a so-called "out-of-range alarm" in which the alarm is triggered when the pressure value is higher than +450 mmHg or lower than +10 mmHg. When an alarm is activated, the blood pump stops. The VPM includes pressure transducing elements and a power supply.

Referring to FIG. 4 and looking at the control system in greater detail, the primary control module 410 operates on a normal electrical supply, and includes a blood pump having a maximum flow rate of 700 ml/minute, an ultrafiltrate pump having a maximum flow rate of 2 1/hour, a Heparin (or similar anticoagulant) pump having a maximum flow rate of up to approximately 10 ml/hour, and pressure monitors and alarms connected to the pressure monitors. The primary control module has mounted thereon a drip chamber holder (Pv) 411 for holding a first (venous) drip chamber 11, a drip chamber holder (P2) 412 for holding a second, e.g., ultrafiltrate, drip chamber 12, and dual blood (e.g., ultrafiltrate and arterial) pumps 413. As illustrated in FIG. 4, an arterial pressure sensor 9 may be provided on the primary control module. Additionally, an atmospheric pressure monitor (unillustrated) may be provided.

The AMU 420 may contain a plurality of commercially available pressure transducers capable of withstanding gauge pressures from approximately 1 atmosphere negative to 3 atmospheres positive. The operating range of pressures from approximately 100 mmHg negative to 200 mmHg positive is preferably accurate to within ±5 mmHg ±2% of the reading. The repeatability within the operating range when this operating range has not been exceeded is preferably within approximately ±2 mmHg.

As shown in FIG. 4, the AMU includes a holder 422 for the device, a drip chamber holder (P1) 423, a second drip chamber holder (P3) 424, as well as a display/user interface and a control section. The user interface can be a relatively simple LCD display, e.g., four lines of 32 characters each, and is formed to allow easy setting of alarm levels by means of the keypad and by presentation of the relevant readouts.

The AMU has appropriate electronics to allow the four transducers to be calibrated at the same two pressures, i.e. a common source can be applied simultaneously to all four pressure transducers and maintained for a duration sufficient to establish and store readings for each transducer at this common established pressure. For example, the two reference pressures may be established by an atmospheric reference and a mercury manometer (or other acceptable secondary standard). The AMU 420 is capable of accepting inputs for upper and lower alarm limits on each of four differential pressures which are important to the device operation. The AMU accepts the inputs via the keypad. These pressure differentials are as follows:

$P_v - P_2$, the minimum transmembrane pressure for the therapeutic device;

$P_1 - P_v$, the blood pressure drop within the therapeutic device;

$P_1 - P_2$, the maximum transmembrane pressure for the therapeutic device; and $P_3 - P_v$, the transfilter pressure drop.

The AMU 420 is also capable of generating alarms according to the alarm set in the manner discussed below.

$P_v - P_2 < 0$ generate AMU audible alarm with system shutdown and AMU panel display suggesting that the potential exists for infusion of cells into the blood stream. Action such as increasing $P_v$ by increasing blood flow, or decreasing $P_2$ by increasing plasma flow may be instituted to achieve $P_v - P_2 > 0$.

$P_1 - P_v$ rising $> 200$ mmHg generate AMU audible alarm with display panel suggesting that if the blood flow has not been increased, then possible clotting should be investigated.

$P_1 - P_2$ rising $> 5$ mmHg generate AMU audible alarm with display panel the same as described above with regard to $P_1 - P_v$ and $P_v - P_2 < 0$.

$P_3 - P_v$ rising $> 250$ mmHg generate AMU audible alarm with display panel suggesting that a transmembrane leak or cellular sloughing be investigated.

$P_3 - P_v$ rising $> 5$ mmHg in 30 seconds, same response as $P_1 - P_2$ rising $> 5$ mmHg with the additional information that the rate of pressure rise was exceeded.

$P_3 - P_v$ exceeding maximum value. Stop entire system. This AMU alarm will also stop the system. It is envisioned that any one or more of the above alarms can be programmed to shut down the system. Additionally, a temporary manual override may be employed to allow pressure readjustment.

There may be a mute capability on the audible alarm, and the system may also be provided with a distinguishing visible alarm (e.g. a flashing light).

The AMU 420 operates from the power supply available from the primary control module 410 and additionally has a battery backup or the like to retain calibrations therein. If the battery backup fails, then the unit automatically displays that recalibration of the pressure transducers is required. The AMU also may be provided with a device for adjusting the monitoring chamber levels during operation of the support system such as a syringe connected to the transducer line of the drip chamber.

Regarding the organ support system tubing sets discussed in greater detail below (and illustrated in greater detail in FIGS. 7–12), the tubing set design is contingent upon the relative positioning of the AMU 420 and the primary control module 410, and is easily adjustable in terms of appropriate lengths and connections to compensate for different designs such that numerous configurations based upon this disclosure are believed to be within the grasp of the ordinarily skilled artisan. Generally, the tubing sets include four portions. The portions which connect to the patient, both arterial and venous, are commercially available, e.g., from CGH Medical, Inc. There are four additional lines, as shown in FIGS. 1–3 and 6–12 and as described below, which are uniquely for the organ support system.

The tubing sets comprise extruded polyvinylchloride (PVC) tubing or the like of the grade typically employed in systems utilized in hemodialysis, therapeutic plasma exchange, and open heart surgery. The pump segments of the tubing preferably are designed to operate at a blood flow rate of approximately 100 ml/minute to 500 ml/minute, and preferably 250 ml/minute, for approximately 120 hours without developing failure resulting in loss of blood by the patient. The molded parts utilized in the tubing sets comprise rigid PVC, Lexan HP resin or other like material and are designed to exhibit long term high strength bonds to PVC tubing in an environment consistent with uses described above. The sterilization method for the tubing sets includes ethylene oxide (EtO) composed of a mixture of EtO and other gases or the like to yield sterilization of the tubing sets. Possible designs of the tubing sets are shown in FIGS. 1–3 and 6–12, and are described below. However, numerous other configurations are envisioned, and thus the configurations shown in the drawings and described herein are merely representative, and not exhaustive.

Referring to FIG. 1 and examining the structure and operations of the present invention in greater detail, the arterial line 2 is shown through which blood is delivered from a double lumen venous catheter (or the like) from the patient. An anticoagulant, e.g., Heparin or the like, is delivered to the arterial line 2 by a syringe 14. Urea, clotting factors, other hepatocyte derived proteins or conversion products, etc. may also be added to the blood. The blood enters an arterial drip chamber 10 (P1), where the precolumn pressure is monitored by the AMU. Blood passes out of the drip chamber and into the organ assist device 1 positioned in a cartridge. A filter 250 or the like (e.g., a commercially available 1-mm mesh filter) may be positioned between the drip chamber 10 and the device 1 to prevent clogging of the device. The organ assist device 1 has an inlet tubing set to which the blood from the arterial line, with or without the anticoagulant, is delivered. The cartridge processes the blood.

Specifically, during the passage through the cartridge, molecules and proteins with a molecular weight cutoff of between 10,000 and 250,000 (and preferably 60,000 to 80,000) are able to diffuse across the cellulose acetate fibers and are exposed to the C3A cells. No cellular material from the blood comes into direct contact with the C3A cells. Small molecules and proteins less than the molecular weight cutoff pass back into the blood.

The cartridge delivers the processed (e.g., modified or detoxified) blood to a venous drip chamber 11, which may be part of an air-in-blood detector, and to the venous line 3. The AMU monitors pressure in drip chamber 11 and displays it as venous pressure. The venous pressure is also independently monitored and displayed by the VPM 430. The AMU also displays the column pressure (P1−Pv) and the primary control module (the BSM-22) monitors for air in the chamber. A flow of blood is drawn from the cartridge and circulated through a recirculation tubing set to check for the integrity of the cartridge and to ensure that the blood has been processed (e.g., detoxified) to an appropriate level.

Specifically, simultaneously with blood flow through the cartridge, plasma is ultrafiltered through the cellulose acetate fibers of the device 1 and into the cell side of the cartridge, where it come in direct contact wit the C3A cells. An ultrafiltrate pump draws plasma across the cellulose acetate fibers of the device 1 and into the ultrafiltrate chamber 12 (P2). The AMU monitors pressure in this chamber and displays the membrane pressure (P1−P2).

Ultrafiltered plasma passes into a second ultrafiltrate drip chamber 12a (P3) and through a cell filter element 5, e.g., a 0.45 μm filter, which is provided to ensure that cells or large molecules do not leak to the patient. Thus, the ultrafiltrate drip chambers are interposed between the outlet of the cartridge and the inlet of the filter as desired. The AMU monitors pressure in the second drip chamber 12a (P3) and displays the filter pressure (P3−Pv).

Pump elements, as described above, may be provided to pump the Heparin at a desired flow rate e.g., 1–10 ml/min, and preferably 1–3 ml/minute. A concentrated form of the Heparin may be used in which case the flow rates may be adjusted accordingly. A pressure sensor 9 is situated in-line between the arterial line access and the Heparin inlet to the arterial line 3. An arterial drip chamber 10 is provided between the Heparin inlet and the cartridge, and a venous drip chamber 11 (associated with an air-in-blood detector if desired) is provided on-line with the venous line 3 between the outlet of the cartridge and the double lumen venous catheter.

Figure 2A:
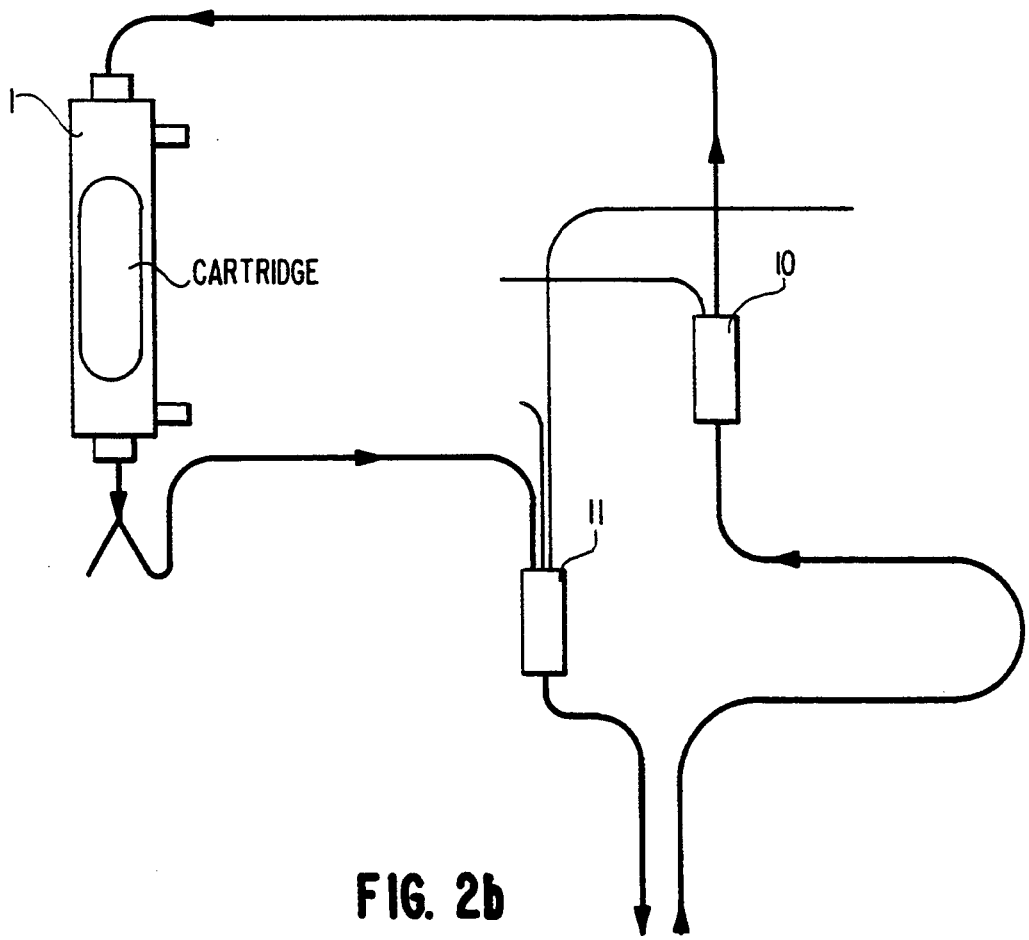
FIG. 2a is a schematic view of the blood circuit of the tubing set used in the system shown in FIG. 1.

Referring to FIG. 2a, a blood circuit of the tubing set used in FIG. 1 is shown, in which an arterial connector has a polyvinylchloride (PVC) tubing with a predetermined diameter e.g., 3/16", to ensure the desired flow rate, connected thereto. A second end of the tubing is connected to the arterial drip chamber 10 which is connected to a second similarly constituted PVC tubing connected to an arterial device connector.

Figure 2B:
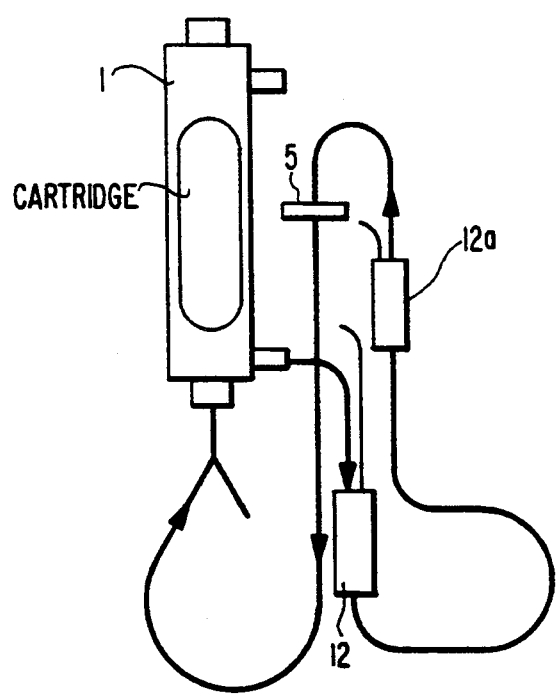
FIG. 2b is a schematic view of the ultrafiltrate circuit of the tubing set used in the system shown in FIG. 1.
Figure 3:
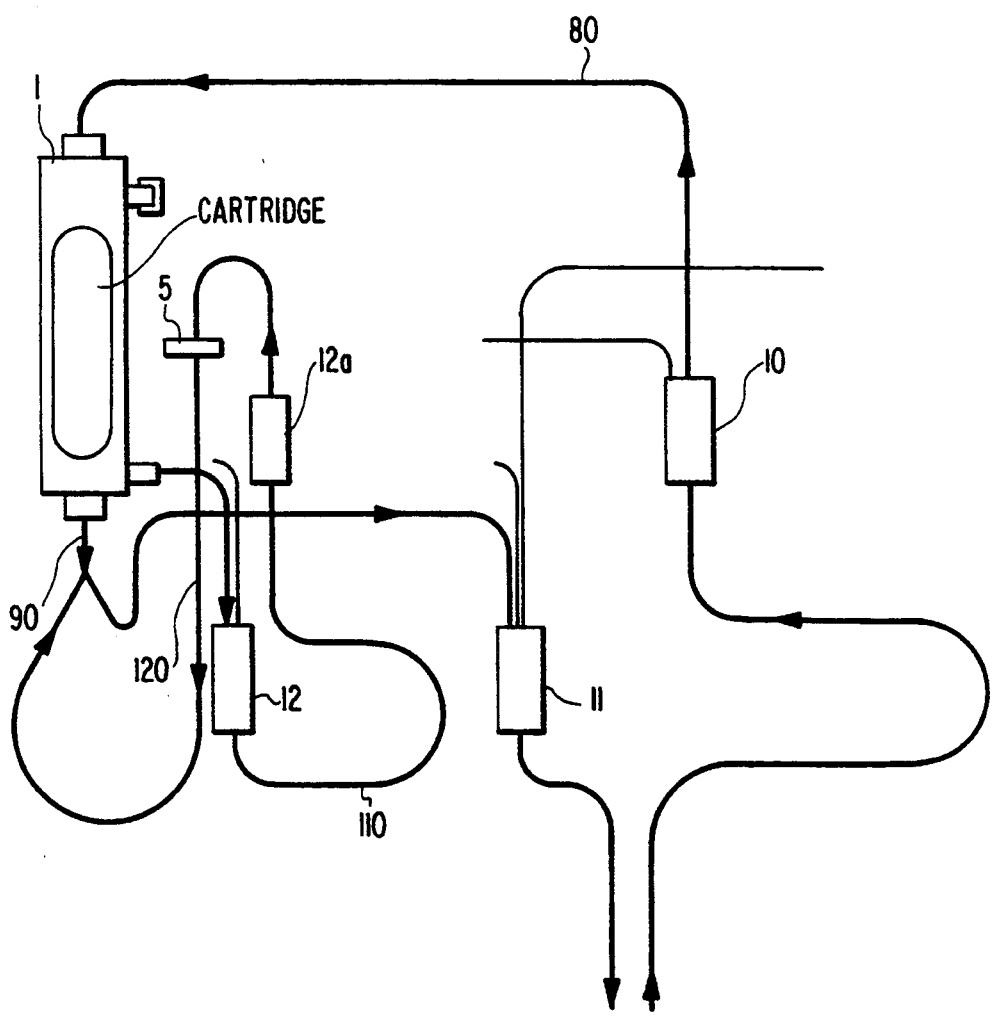
FIG. 3 is a schematic of the combined tubing sets assembled for use with the organ support system shown in FIG. 1.

Referring to FIG. 2b, the ultrafiltrate circuit of the tubing set used with the system shown in FIG. 1 is shown. Specifically, a filtrate connector is connected to an input end of the first ultrafiltrate drip chamber 12. The second ultrafiltrate drip chamber 12a is connected to the first ultrafiltrate drip chamber by a tubing. An outlet of the second ultrafiltrate drip chamber has a 3/16" PVC (or the like) tubing connected to the filter 5 (e.g., a single filter or a double filter). The filter 5 senses and contains any leakage of cells from the extra-capillary space of the organ assist device 1. Either of these filters (i.e., the single or the double filter) may be connected to an alarm unit of the system's control module.

Figure 6:
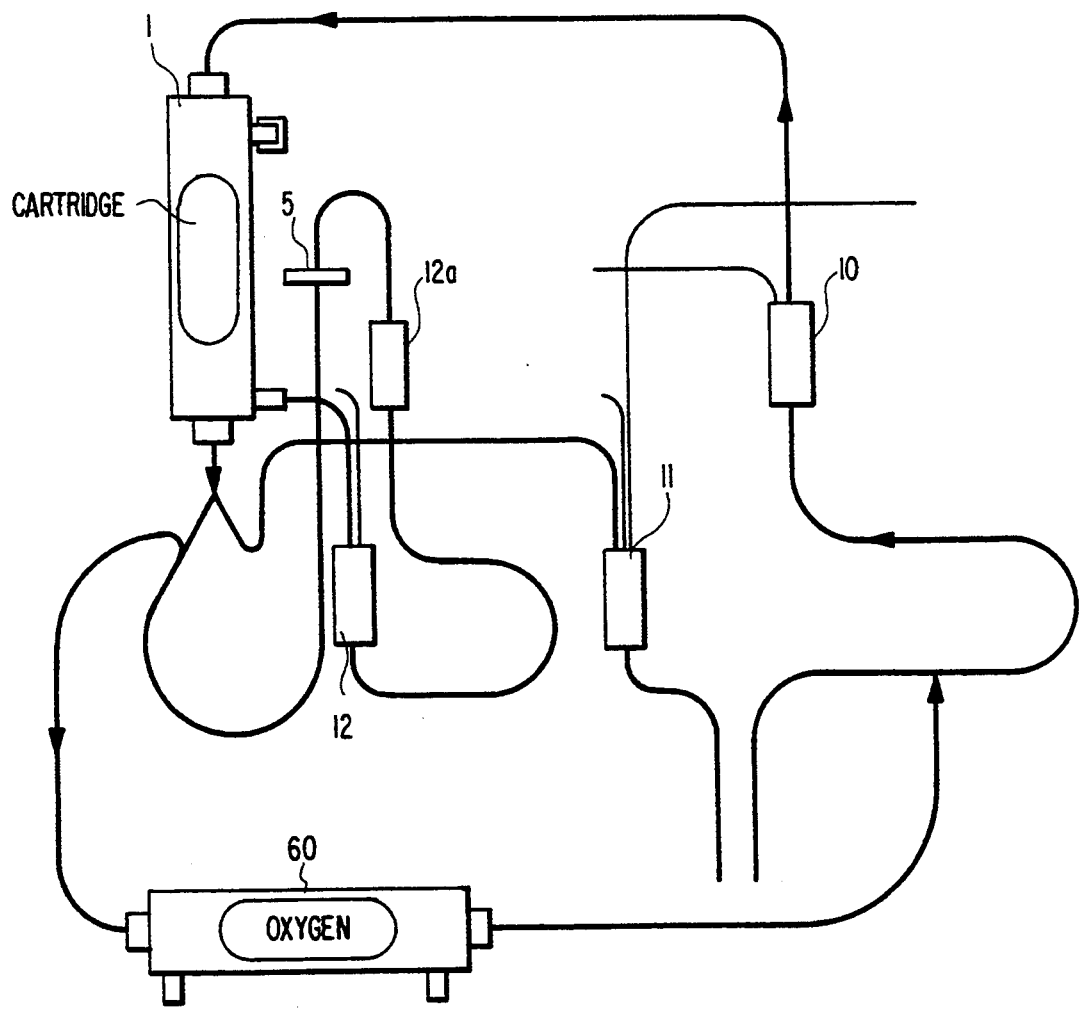
FIG. 6 is a schematic view of a tubing modification which allows a cartridge to be oxygenated.

As shown in FIG. 6, the outlet of the filter 5 may be connected to a first three-port (e.g., Y-shaped or T-shaped) tubing fitting having a fitting for an oxygenator line at one end for connection to an oxygenator 60 discussed in detail below. For convenience, a Y-shaped connector is illustrated in the drawings and described hereinafter. A second Y-shaped tubing fitting may be connected to the first Y-tubing fitting, and may include a venous tubing fitting at a first end and a venous connection device at a second end.

The tubing and connections thereof are preferably capable of withstanding positive pressure (lumen to exterior) of 3 atmospheres (2,300 mmHg) and negative pressure of 0.75 atmospheres without suffering catastrophic failure or developing leaks between the interior and exterior of the tubing set. This design results from the consideration that the typical pumps and tubing, used for extracorporeal treatment, reach their delivery limits at about 0.7 atmospheres negative pressure and 1.5 atmospheres positive pressure. The pressure limits established bracket these limits and provide a reasonable safety margin.

The recirculation flow, e.g., the extraction flow rate, for the recirculation tubing set is between 5 and 120 mls/minute, and preferably from 20 to 80 ml/minute. The parameters of the extraction flow rates are based on the consideration that by using such a flow, it is ensured that a broken fiber will not result in flow from the extracapillary space to the intracapillary space within the therapeutic device. This flow can also be defined in terms of a fraction of the blood flow. For example, the extraction flow rate is within a range of from 5% to 30% of the blood flow rate, and preferably from 10% to 20% of the blood flow rate. The operator is preferably provided with a table of recirculation flow rates correlated with blood flow rates, or alternatively it is envisioned that such could preferably be stored in a memory of the controller.

The arterial line 2 has an interlock with an arterial pressure alarm. This feature may be included in the AMU. The venous tubing set also has a unique integration with the primary control module 410 e.g., the BSM-22. In the case of the venous line, this may include the air-in-blood (AIB) detector system. However, instead of this configuration, the AIB can be added to the AMU.

As mentioned above, pressure sensors may also be employed in the system for added safety. For example, as shown in FIG. 1, the pressure sensor 9 may monitor the pressure of the arterial blood being pumped from the patient to the device 1. Additionally, a pressure sensor may monitor pressures at the inlet tubing connected to device 1 after Heparin or a like anti-coagulant is pumped into the arterial line. Other pressure sensors 8 may be included at the outlet venous line to measure the return of fluid to the patient, as well as in the recirculation tubing set at various locations for added safety. Thus, the pressure sensors allow for the monitoring of both the access and return pressures of the patient, and the pressure across the device to detect plugging or rupture problems thereof. Furthermore, pressure sensors on each side of the filter can monitor for any release of cellular or large particles from the device and pressure sensors on the ECS can monitor a rise in the ECS pressure which will result in flow of fluid from the ECS to the ICS.

A hemoglobin detector 13, shown in FIG. 1, may be utilized to indicate any leaks in one of the hollow fibers of the device 1. The hemoglobin detector can also serve to indicate any loss of cells or particles from the extracapillary space as these cells scatter the light and reduce the monitor's output correspondingly. Further, the hemoglobin monitor can be coupled to various alarm circuits to indicate that operator attention is required. The pressure sensors 8 can be incorporated into similar alarm systems, or have an alarm system dedicated thereto. Both the hemoglobin detector and the pressure sensors, as discussed above, can be coupled to the controller, and can be used to shut down one or more pumps of the closed loop system. The optical hemoglobin detector is preferably capable of detecting blood losses to the recirculation line of 1 part packed red cells in 60 parts of plasma. This detection method should preferably operate for both losses which result in intact red cells in the detector or for the specified quantity of cells totally hemolyzed.

If an optical cell or the like is required to accomplish detection of the hemoglobin, then the connections to the optical cell must be compatible with the selected tubing of the recirculation line. The optical cell should be reliably mounted into the electromechanical equipment to permit manipulation of tubing sets and equipment without compromising either accuracy or reliability of operation. The optical cell is conventional, and is believed to be commercially available. Detection of the leakage of red blood cells into the extra capillary space may be performed by measuring the pressure differential across the filter.

An oxygenator 60, as shown in FIG. 6, may also be provided with a corresponding oxygenator shunt. The oxygenator and the oxygenator shunt are commercially available from Unisyn Fibertec, Inc. and Lifemed, Inc., respectively. The oxygenator shunt allows the inclusion of an oxygenator to permit assessment of the patient's ability to be weaned from the system without compromising the possibility of returning to the system. This is readily achieved by providing attachment ports for the shunt so that it can rapidly be attached. The oxygenator performs the function of providing oxygen to the cells and allows the patient to be weaned by bypassing the organ assist device when the shunt is connected. Thus, the patient may be functionally, but perhaps not physically, detached from the system. The required supply of nutrients and the "respiration" for the cell line must come from other sources such as fresh culture media and an oxygenator. This capability will require that the patient lines be flushed of blood and then be loaded with tissue culture fluid. Fresh tissue culture fluid could also be infused continuously as is done during preparation of the cartridges.

One method of attachment of the oxygenator 60 is shown in FIG. 6, in which a first connection is a part of the arterial line 2, and is connected to a connector of the oxygenator. A second end of the oxygenator is connected to part of the recirculation line set which is shown in greater detail in FIG. 3. The setup and connection of the oxygenator to the inventive configuration is believed to be well within the grasp of one of ordinary skill in the art.

Furthermore, the system configuration can be modified to include an arteriovenous fistula in which the pump connected to the arterial line is obviated. Further, the configuration can be adapted for use with a single needle access by adding a reservoir at either end of the cartridge and including a blood pump on the return line.

The blood flow rate may be adjustable within the range of 0 to 500 mls/minute. The rationale for this is several fold. It is well established that continuous hemodialysis is effective at blood flows of 150 mls/minute. This is to be contrasted with the resting normal renal flow rate of about 1,000 mls/minute. It is believed that the liver has less reserve capacity than the kidneys, and hence the maximum flow rate is a higher fraction of the resting normal hepatic blood flow rate of about 1,500 mls/minute. It is also well established that such extracorporeal flow rates are achievable with standard blood access devices, e.g. single or dual lumen subclavian catheters. With higher blood flow rates, the therapeutic effect may be enhanced. Efficacy of this device has been demonstrated at flows of 75-100 ml/minute (see, e.g., Kelly et al., "Assessment of An Extracorporeal Liver Assist Device," *Artificial Organs*, 1992, vol. 16, pp. 5-9; Sussman et al., Reversal of Fulminant Hepatic Failure Using an Extracorporeal Liver Assist Device," *Hepatology*, 1992, vol. 16, pp. 60-65.).

Figure 7:
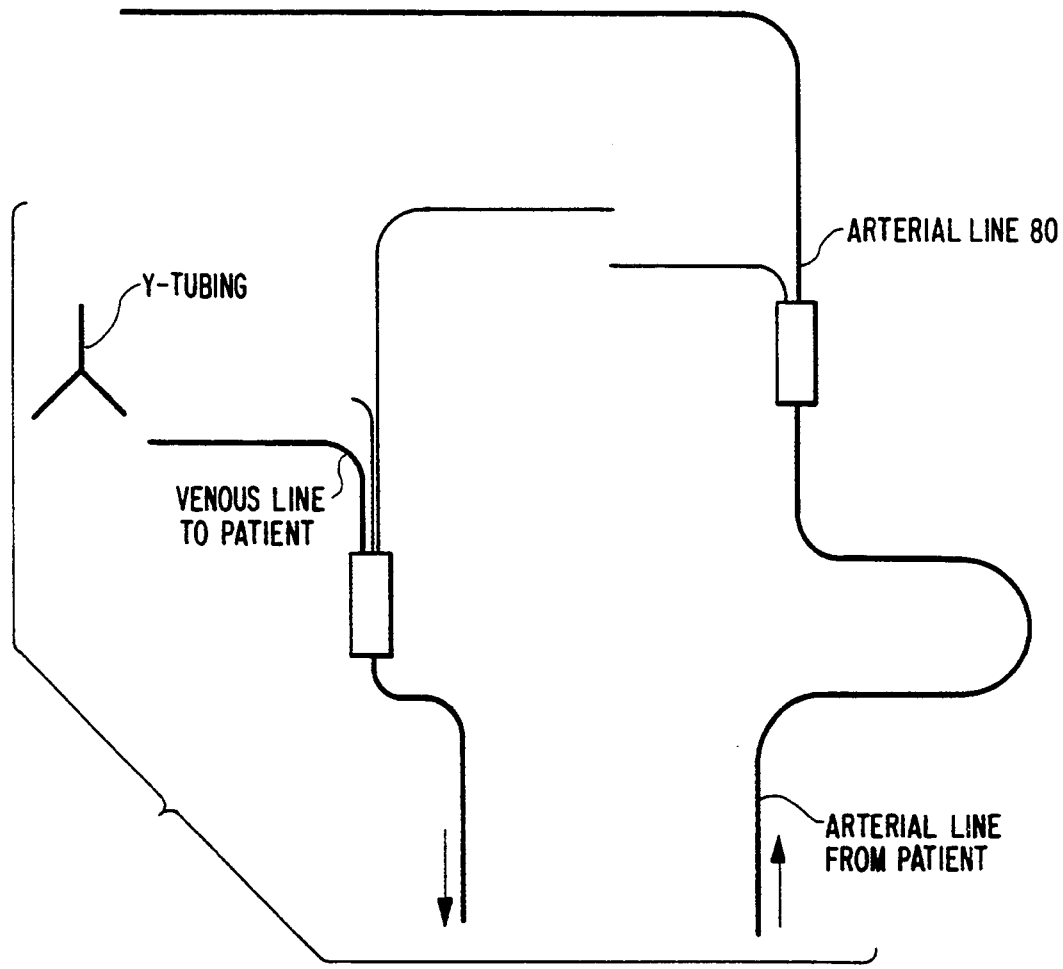
FIG. 7 illustrates the overall blood circuit.
Figure 10:
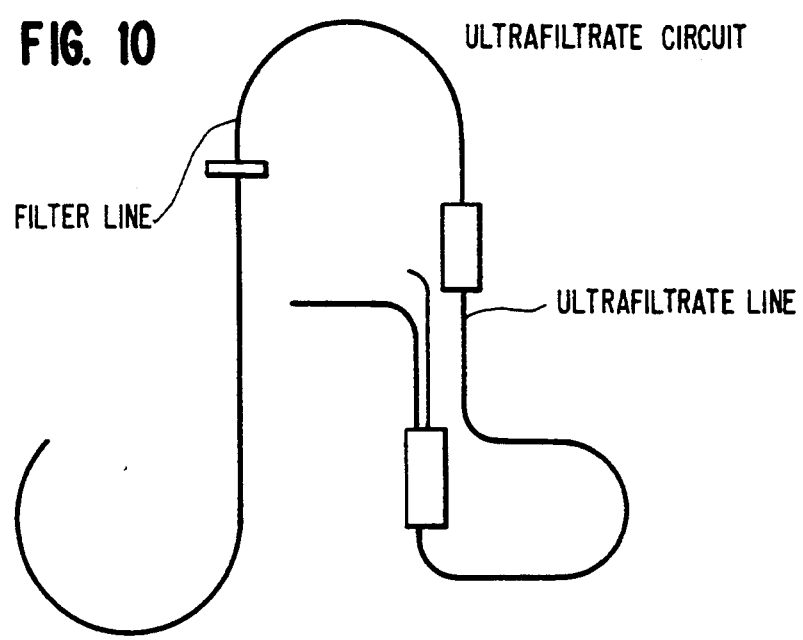
FIG. 10 illustrates the overall ultrafiltrate circuit.

Referring to FIGS. 7-12 and examining the organ support system tubing sets in greater detail, FIG. 7 shows the overall blood circuit, and FIG. 10 illustrates the overall ultrafiltrate circuit. As mentioned above, the arterial line leading to the connection at the first drip chamber 10 is commercially available from CGH, Inc. Likewise, the venous line leading from the second drip chamber 11 back to the patient is also commercially available from CGH, Inc. The arterial line leading from the first drip chamber 10 to the organ assist device and the Y-shaped connector tubing are unique to this invention. Likewise, the ultrafiltrate circuit is unique to this invention, and includes an ultrafiltrate line and a filter line, as shown in greater detail in FIGS. 11 and 12.

Figure 8:
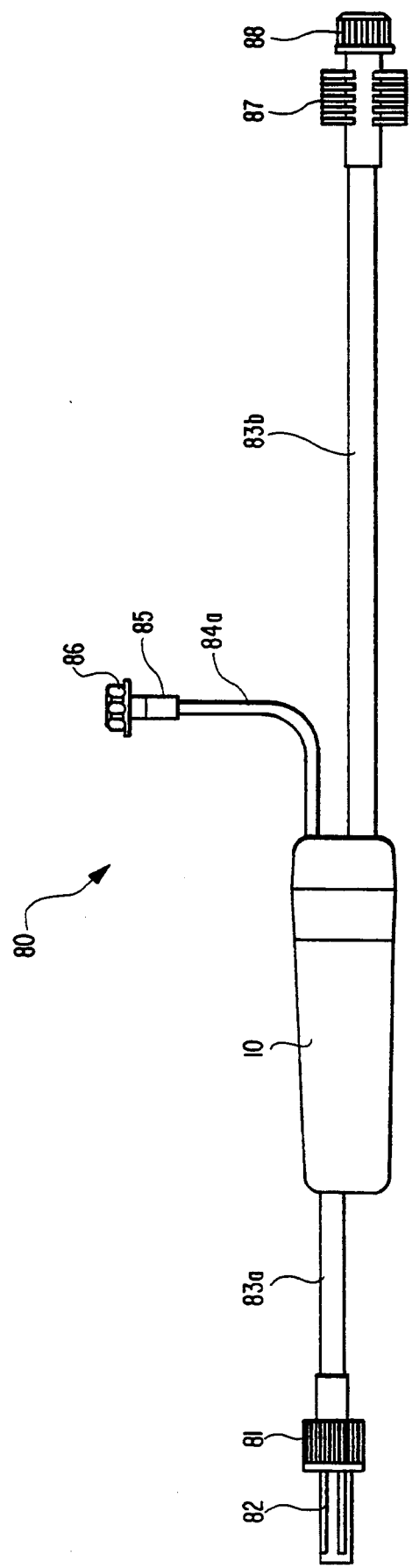
FIG. 8 illustrates the arterial line of the blood circuit leading between the drip chamber assembly and the cartridge.

Turning to FIG. 8, the arterial line 80 is illustrated leading between the first drip chamber (D/C) 10 and the organ assist device. The arterial line includes a male DIN connector 81 and a protective cap 82 press-fitted thereto. A reverse flow D/C assembly 10 is coupled to a PVC tubing 83a. The reverse flow D/C assembly 10 has a second end coupled to a PVC tubing 84a and a second PVC tubing 83b. PVC tubings 83a, 83b may have an outer diameter of 0.262 mm and an inner diameter of 0.187 mm. PVC tubing 84a may have an outer diameter of 0.125 mm and an inside diameter of 0.062 mm. PVC tubing 84a is coupled to a female locking luer connector 85. A male locking luer cap 86 is twisted onto the female locking luer connector. A locking dialyzer connector 87 is coupled to the second PVC tubing 83b. The connector 87 is in turn secured by a dialyzer cap 88 which is press-fitted to the second PVC tubing 83b.

Figure 9:
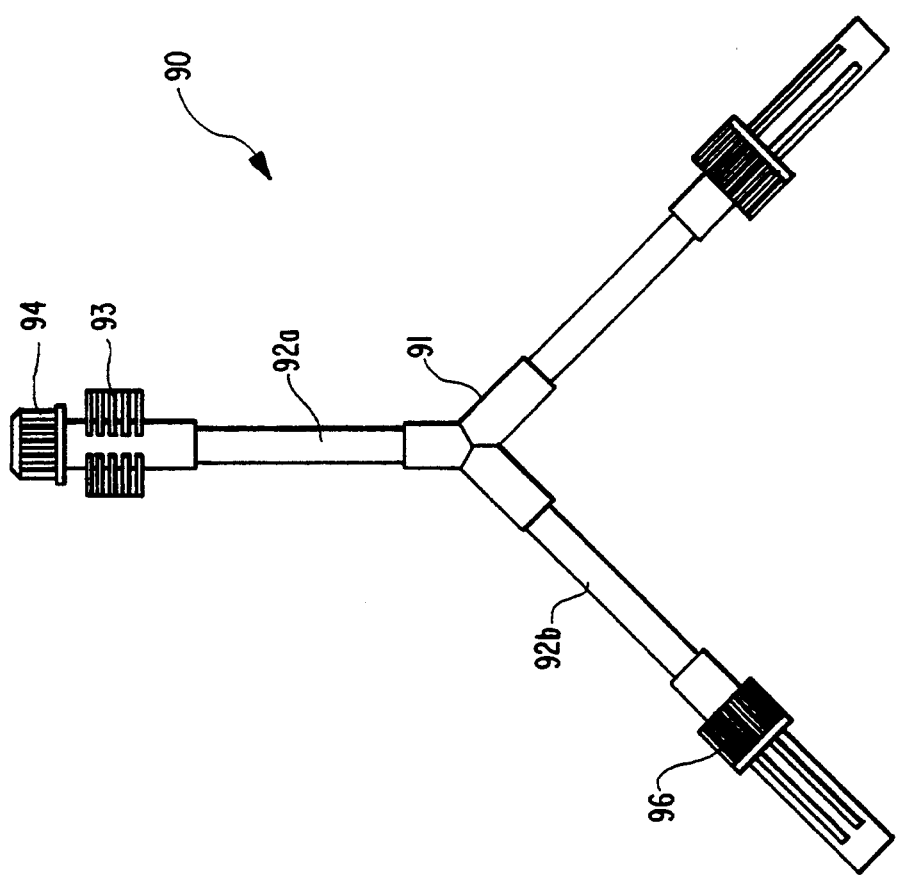
FIG. 9 illustrates the three-port (e.g., Y-shaped) tubing connection of the blood circuit.

FIG. 9 shows the Y-connector line 90 and its arrangement. A Y-connector 91 has a first end coupled to a PVC tubing 92a which in turn is coupled to a locking dialyzer connector 93 having a dialyzer cap 94 press-fitted thereon. A second end of the Y-connector 91 is attached to a second PVC tubing 92b which in turn is coupled to a male DIN connector 95. Connector 95 has a protective cap 96 press-fitted thereto. A third end of the Y-connector 91 has an arrangement similar to that of the second end. All the junctions are suitably bonded together, e.g., by cyclahexanone bonding, etc.

Referring to FIG. 10, an overall schematic of the ultrafiltrate circuit is shown. As mentioned above, the two lines making up the ultrafiltrate circuit include the ultrafiltrate line (shown in greater detail in FIG. 11) and the filter line (shown in greater detail in FIG. 12).

Figure 11:
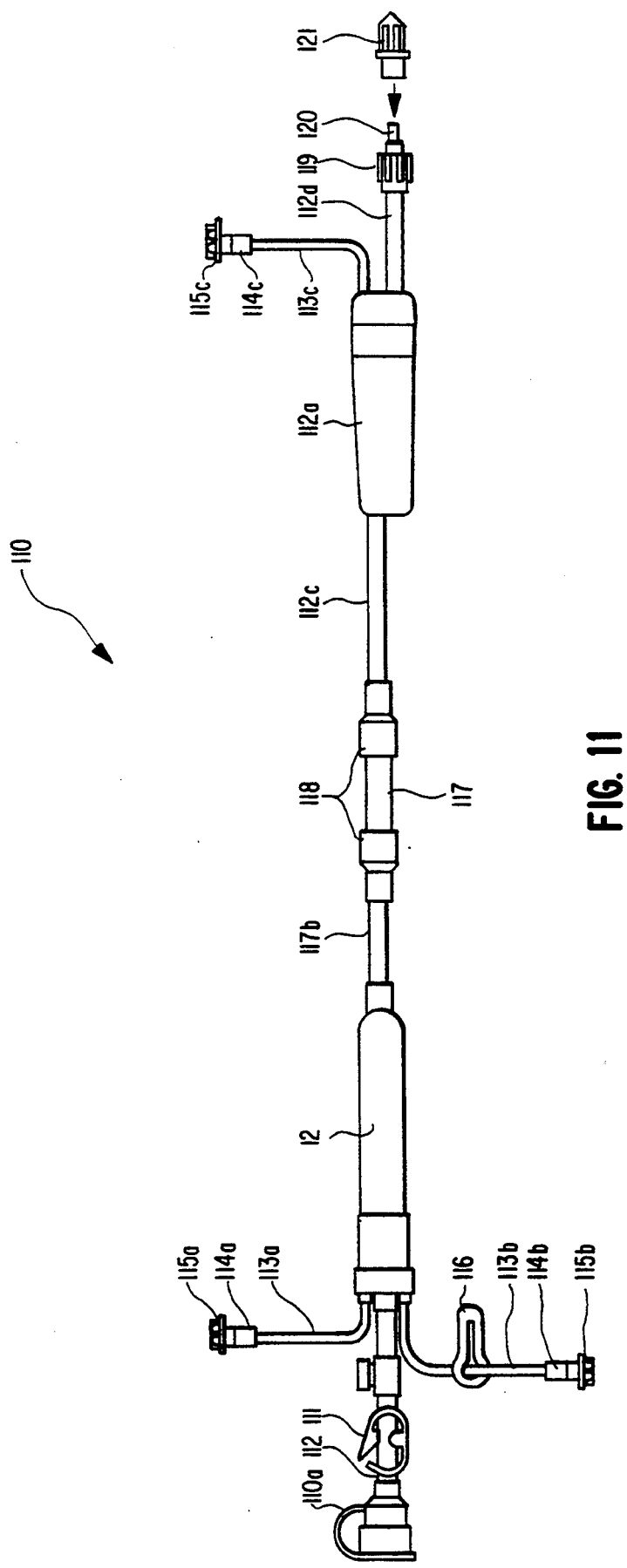
FIG. 11 illustrates the ultrafiltrate line of the ultrafiltrate circuit.

Turning to FIG. 11, the ultrafiltrate line 110 is coupled to an outlet of the organ assist device, and includes a Hansen-style dialysate connector 110a which in turn is coupled to a duraclamp 111 which is slidably received on a length of PVC tubing 112. The PVC tubing 112 may have an outer diameter of 0.262 mm and an inner diameter of 0.187 mm. A second end of the PVC tubing 112, which may include an injection site (unreferenced), is coupled to the drip chamber assembly 12 which may be a three-port drip chamber assembly. Drip chamber 12 also has input thereto a PVC tubing 113a which in turn is connected to a female locking luer connector 114a which has a male locking luer cap 115a secured thereto. A second PVC tubing 113b is also input to the drip chamber. PVC tubings 113a and 113b may have an outer diameter of 0.125 mm and an inner diameter of 0.062 mm. PVC tubing 113b is coupled to a slide clamp 116. A second end of the PVC tubing 113b is connected to a female locking luer connector 114b which has a male locking luer cap 115b secured thereto.

The outlet of the drip chamber 12 is coupled to a PVC tubing 112b which in turn is coupled to a pump segment 117 by a pump connector 118 which in turn is coupled to a PVC tubing 112c. The outlet of the PVC tubing 112c is coupled to an inlet of a drip chamber 12A. Drip chamber 12A may be a reverse-flow drip chamber assembly. The outlet of the D/C assembly 12A is coupled to a PVC tubing 113c having a female locking luer 114c and a protective cap 115c thereon. Additionally, a PVC tubing 112d is coupled to the outlet of the drip chamber 12A and includes a fistula locking hub 119 and a fistula locking luer 120 coupled thereto. A vented luer slip 121 is press-fitted to the locking luer 120.

Figure 12:
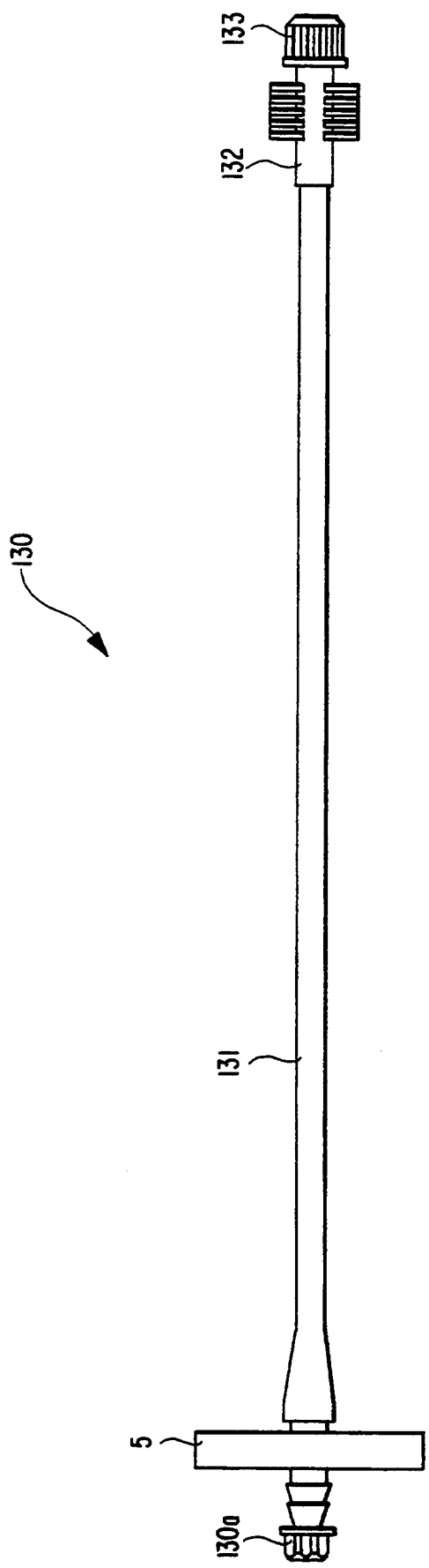
FIG. 12 illustrates the filter line of the ultrafiltrate circuit.
Figure 13:
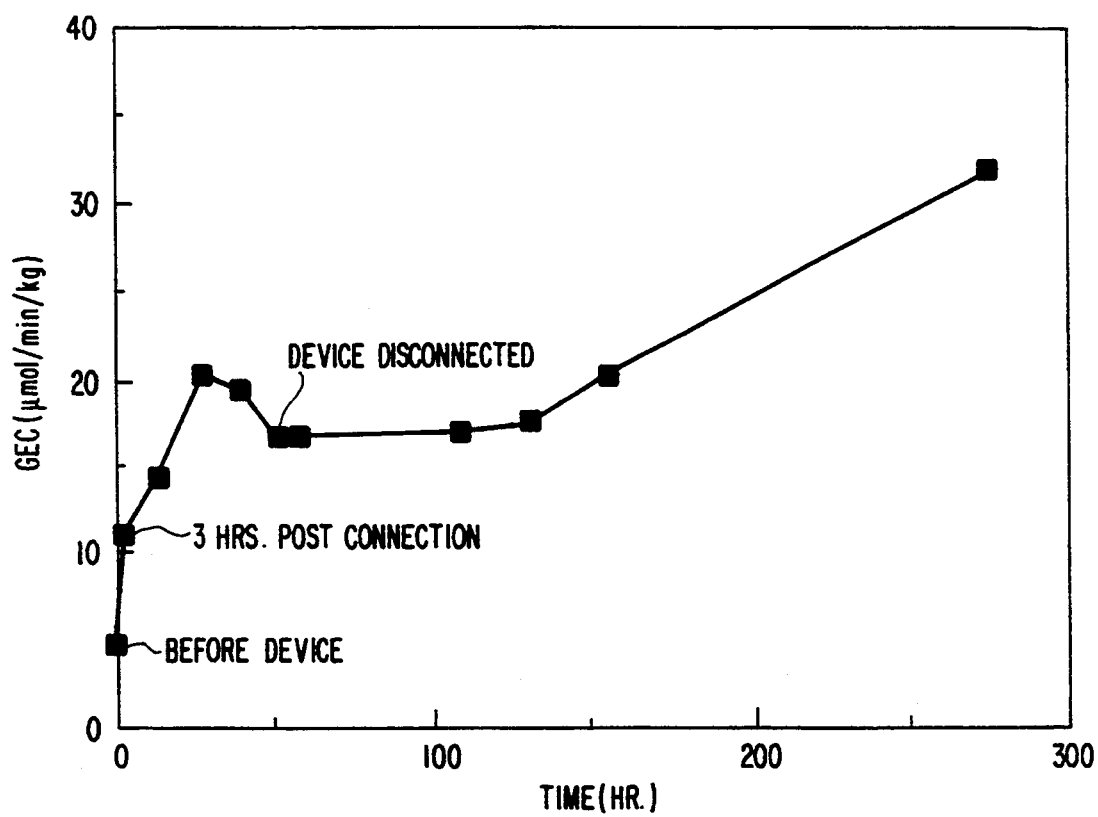
FIG. 13 is a graphical illustration of the results of utilizing the organ assist system according to the present invention with a 12-year old girl, and, specifically, the increase in her Galactose Elimination Capacity (GEC) during treatment with the system according to the present invention.

Turning to FIG. 12, the filter line 130 is shown having a vented luer cap 130a which is coupled to the ultrafiltrate line by being press-fitted thereto. The cap 130a is coupled to an inlet of the filter 5. The outlet of the filter has a first end of a PVC tubing 131 stretched thereover. A second end (i.e., the outlet) of the PVC tubing 131 is in turn coupled (e.g., cyclahexanone bonded) to a locking dialyzer connector 132. Connector 132 has a dialyzer cap 133 press-fitted thereon. The locking dialyzer connector is adapted to be connected to one of the inputs of the Y-connector described above.

The configurations of the tubing sets are merely representative, and can be modified as necessary. Along these lines, certain modifications may be possible for long-term dialysis. One possibility would be to make portions of the tubing sets easily removable (i.e., modular) and interchangeable. For example, the ultrafiltrate line and the PVC tubing line between the drip chamber 10 and the organ assist device 1 may be replaced as necessary. Further, the PVC tubing line between the drip chamber 11 (PV) and the patient may be replaced as necessary. Additionally, it is envisioned that mesh filters or the like may be positioned at the outlet of the drip chamber 10 to prevent clots from embolizing to the organ assist device 1.

To establish operation of the system, ordinary medical procedures are conducted, and equipment setup is believed to be well within the grasp of the ordinarily skilled artisan. Briefly, the operator responsible for the setup of the equipment will load the blood tubing set onto the control unit, appropriately thread the pump headers into the pumps, attach the pressure monitoring tubing to the pressure monitor connections, set the alarm settings to the values appropriate to the priming mode, fill the anticoagulant (e.g., Heparin) syringe with the prescribed Heparin dosage, attach the Heparin syringe to the tubing set, secure the Heparin syringe to the control unit, and attach the priming solution to the tubing set arterial connectors. The priming solution may be normal saline.

For blood access, the physician in charge of the procedure will establish an appropriate procedure and perform the blood access. This blood access must be capable of delivering the blood flow rate mentioned above required to achieve the desired therapeutic input upon the patient. This blood access must be appropriately anticoagulated by Heparin or the like as discussed above. The principles of operation of the therapeutic device depend upon unhindered passage of certain blood borne materials to the extracapillary space and similar passage of solutes from the extracapillary space to the blood. Compromising this carrying capacity due to inadequate anticoagulation is to be avoided. Of particular concern at the initiation of circulation is coagulation created by stasis within the access during preparation.

The first connection to be made is the patient access line e.g., arterial line. The priming solution is ported into the tubing sets arterial connection at a rate sufficient to ensure that the return line and return line connection are free of trapped air. When the connection is made, flow of priming solution is halted so that the physician can manipulate the tubing to ensure that there is not an unacceptable amount of air at the connection. The arterial line is then connected.

To initiate the procedure, the bypass pump is started at the protocol flow rate and the recirculation (e.g., bypass) loop is visually checked for drip chamber levels, leaks, and evidence of blood cell leaks. The recirculation pump is started. The venous line is unclamped, and the Heparin pump is started at its initial setting. The blood pump is started at a low flow rate and the various attachment points are checked for leaks. The pressure monitoring chamber levels are examined and adjusted if necessary. To continue the procedure, the operator or attendant personnel should periodically examine the fittings for leaks, the bypass tubing set for evidence of blood cell accumulation, and the monitoring chambers for appropriate levels. The monitoring chamber levels should be readjusted if they vary by more than 0.5 cm from the nominal level, the nominal level being 50% or higher of the drip chamber. Frequent adjustment of a given monitoring chamber level should motivate the operator to thoroughly examine the tubing for minute leaks. The Heparin syringe should be monitored for the amount remaining and replaced as appropriate.

When the procedure is to be terminated, and the setup broken down, the blood pump, the recirculation pump, and the Heparin pump are stopped in turn, and the arterial access clamped. The blood remaining in the system is returned to the patient per protocol using either fluid or air displacement, and the venous access clamped. At this point, the control unit with the attached tubing set and therapeutic device can be removed from the ICU or area in which it has been used.

Other components of the system may include automated blood-in-filtrate detectors, or individual dedicated monitoring chamber level adjustments.

The major safety issue in using the system is rupture of the membranes. There are two issues concerning a ruptured membrane. A first issue is the possibility of the cultured cells detaching from the walls of the device and infusing into the blood stream. Secondly, the loss of blood by the patient is an issue.

Regarding a potential cell line leak to the blood system, the unit is to be operated with the $P_v - P_2$ positive, i.e., the flow will always be in the direction from blood space to the extracapillary space. Fiber rupture is extremely rare (i.e., approximately less than 1/100,000 cartridges). With the integrity of the fibers intact (i.e., in the absence of a fiber rupture), this flow causes a modest ultrafiltration which passes through the recirculation pump and through the filter(s) of the recirculation loop. A rise in the pressure gradient will trigger an alarm and stop the blood pump until corrective action is taken. When blood pumping ceases, the therapeutic device is isolated from the patient. The therapeutic device can then be replaced along with the recirculation line. Thus, no cells will have entered the patient's blood stream unless the filter or filters have failed.

Regarding the safety aspects of a membrane rupture respecting potential patient blood loss, a concern in CIHD described briefly above is that a blood leak to dialysate may result in unacceptable blood loss. This is largely due to the high dialysate flows (on the order of 500–1,000 mls/minute) which, if replaced by the patient's blood, would result in rapid exsanguination of the patient. This concern has led to the use of hemoglobin detectors in the dialysate pathway.

In the present invention, this is not a major concern since the dialysate ultrafiltrate flow is on the order of 20–80 ml/min; the ultrafiltrate is returned to the patient and hence no net blood loss; and the cell filter is occluded with as little as 0.1 ml/min. Hence, blood loss is not a major concern and does not have the same significance as in CIHD.

Described above is the present invention which relates to an organ support system and method for sustaining a patient. As mentioned above, the embodiment of the invention discussed in detail is directed to the liver, but it is envisioned that the support system can be used for other organs. The organ support system has a cell line which mimics the function of a specified bodily organ e.g., liver, kidney, etc. The cell line is placed in a hollow cartridge and blood from a patient is passed through the inter-capillary space of the cell line allowing molecules to pass through the semi-permeable membrane for conversion and detoxification in the extra-capillary space. The system can be easily checked for leaks and modification (e.g., regulation, detoxification, etc.) levels of the blood, while ensuring safety of the patient.

The present invention offers many advantages over the conventional systems. For example, the inventive system has a closed loop configuration, and does not require the use of a dialysate. Thus, patient fluid balance is not an issue since there is no appreciable shifting of the fluid balance.

Additionally, the present invention is directed to fluid modification, e.g., separation of molecules/cells, as opposed to only plasma separation. Indeed, many treatment systems require plasma separation prior to cell diffusion. Thus, the present invention avoids the problems of plasma separation and can be configured to exclude the presence of antibodies in the ECS. Further, the pore size of the device allows proteins on the order of 10,000 to 250,000 (molecular weight), and preferably 70,000. Thus, the pore size of the fibers will admit molecules from 10,000 to 250,000, and preferably 70,000.

Further, the flow rates utilized with the inventive configuration are higher than those employed in the conventional systems, resulting in the detoxification of the patient's fluids being performed much more quickly than in the conventional systems. Still further, as mentioned above, the invention provides a much safer apparatus, and one in which the patient is much less likely to receive toxic fluid products which have been recirculated.

Other advantages of the present invention include providing a new and improved support system and method for sustaining a bodily organ such as a liver having high flow rates and which can be monitored for patient safety; providing a device for implementing treatment with an organ support system which maintains viability of cells in a cartridge during treatment; providing a system in which a pressure gradient from the ICS to the ECS is maintained continuously during therapy; providing a support system which is designed such that a dialysate is not required to regulate blood and the like; providing a closed loop system in which there is no appreciable shifting in the patient's balance (other than the fluid recirculated in the extracorporeal circuit) and which allows continuous and accurate measurement and control of the volume of fluids removed from the patient; providing an organ support system which can be operated continuously; providing an apparatus in which blood returned to the patient is sterile and pyrogen-free; providing an apparatus in which an ultrafiltrate is returned to the patent's blood stream in a sterile and pyrogen-free manner; providing an organ support system which is regulated such that treatment is automatically discontinued in the event that an untoward event occurs; providing an organ support system which does not require continuous human monitoring other than to respond to an alarm; and providing an organ support system which is capable of supporting a metabolically-active device (such as an artificial organ) during varying periods of disconnection from the patient in order to allow such activities as testing of the patient's own organ function.

The present invention will be further described by way of the following Example to illustrate aspects of this invention. The Example is not intended to limit the scope or applicability of this invention.

TEST RESULTS

Example I

Recovery from Syncytial Giant-Cell hepatitis (SGCH) following treatment by the inventive system as described above and using an extracorporeal liver assist device has been illustrated, as discussed below.

SGCH has been reported as a cause of severe hepatitis with little hope of spontaneous recovery. However, the inventive system was used with a twelve year-old girl having a viral syndrome which was initially treated with ibuprofen and promethazine HCl. Multisystem disease developed over the following week with persistent fevers, eosinophilia, pneumonitis, dermatitis, myositis, pancreatitis, nephritis, and hepatitis. The patient developed hepatic encephalopathy on day 19 of her illness, and became comatose one week later. Liver biopsy revealed vacuolated hepatocytes, syncytial cells, and cytoplasmic inclusion bodies consistent with a paramyxovirus infection. The patient was coupled to and treated with an organ support system according to the invention, at Texas Children's Hospital, Houston, Tex.

Specifically, the system used included an Auxiliary Monitoring Unit, a Venous Pressure Module, and a Primary Control Module (BSM-22) with associated pump circuits, and arterial, venous, and recirculation tubing sets connected with an extracorporeal liver assist device (ELAD) containing 200 g of cultured human hepatocytes. Equipment setup was as described above. Specifically, the patient was connected to a double lumen catheter and the system incorporated the organ assist device (i.e., the ELAD having a C3A line, commercially available from Baylor College of Medicine, and housed in an Althin CD Medical, Inc. Altraflux cartridge). The ELAD containing the 200 g of cultured human hepatocytes had an input coupled to an arterial line leading from the patient and an output connected to a venous line returning the modified blood to the patient. Blood flows were 100 ml/min. and a Heparin line was connected to the arterial line at a flow of 2 ml/min. (concentration of Heparin was 200 units/mi.

The patient was treated with the system employing the ELAD for 58 hours, and the system/ELAD had an immediate effect on her Galactose Elimination Capacity (GEC) which increased from 4 to 11 $\mu$mol/min/kg, as shown in FIG. 7. Steady improvement was seen over the next two days, GEC was 16.5 at the conclusion of treatment, and increased to near-normal levels by 10 days. Her mental status lagged behind the GEC, but returned to normal. Cholestasis and elevated transaminases were evident at discharge, but these continue to improve and are normal at the 6-month time point.

The following conclusions can be made based upon the test results above.

1. Survival was highly unlikely in view of the etiology of the patient's disease, her advanced encephalopathy, and her low GEC.
2. The metabolic capacity of the system in general and the ELAD in specific was demonstrated by a significant increase in the GEC of the patient during the course of treatment.
3. Recovery of the patient's own liver function was documented by serial GEC assays, and by her eventual recovery.
4. Recovery from advanced stages of FHF is possible if the patient is supported through the critical phase of the illness.

While certain preferred embodiments have been shown and described, many changes and modifications within the spirit of the invention will be apparent to those of working skill in this technical field. Thus, the scope of the invention should be considered as limited only by the appended claims.

What is claimed is:

1. An organ support system adapted for use with a patient, comprising:
    an organ assist device for receiving fluid from the patient and designed to pass said fluid therethrough to modify said fluid;
    a first line having first and second ends, said first end being connected to an outlet of the patient for drawing fluid therefrom, and said second end being connected to an input of said organ assist device;
    a second line having first and second ends, said first end being connected to an output of said organ assist device, and said second end being connected to an input of said patient to return said fluid having been drawn from said patient and having been modified by said organ assist device;
    a third line having first and second ends, said first end being coupled to said organ assist device for drawing a predetermined volume of fluid therefrom, and said second end being coupled to said second line; and
    a control system for automatically controlling said fluid flow of said patient and measuring a characteristic of said fluid, said system having a closed loop configuration formed by said first line, said second line, and said third line, said control system comprising means for continuously maintaining a pressure differential between said third line and said second line.

2. An organ support system according to claim 1, wherein said organ assist device comprises a cell line inserted into a hollow fiber cartridge having a semipermeable membrane and forming an extra-capillary space for perfusion of cells of said fluid therethrough for conversion and modification of said fluid.

3. An organ support system according to claim 1, further comprising a filter member coupled to said third line, a pressure detector coupled to said first line, a plurality of pressure detectors coupled to said third line, and a pressure detector coupled to said second line.

4. An organ support system according to claim 1, wherein said organ assist device comprises a semipermeable membrane having a molecular cutoff of between 10,000 and 250,000.

5. An organ support system according to claim 1, further comprising an injecting member coupled to said first line.

6. An organ support system according to claim 5, wherein said injecting member injects an anticoagulant into said first line.

7. An organ support system according to claim 1, further comprising a detector coupled to said organ assist device which detects a loss of cells from said organ assist device.

8. An organ support system according to claim 1, further comprising an oxygenator coupled to said first line and said third line.

9. An organ support system according to claim 1, further comprising a pumping device coupled to said first line.

10. An organ support system according to claim 1, further comprising a pumping device coupled to said third line.

11. An organ support system according to claim 1, further comprising a fourth line coupled to said first line, an injecting device coupled to said fourth line, and a pumping device coupled to said fourth line.

12. An organ support system according to claim 1, wherein said third line comprises a recirculation cell line.

13. An organ support system according to claim 1, wherein a flow rate of fluid from said patient through said organ assist device is 75 ml/min to 500 ml/min, and preferably from 100 to 250 ml/min.

14. An organ support system according to claim 1, wherein an extraction flow rate of fluid from said organ assist device through said third line is from 5 ml/min to 120 ml/min.

15. An organ support system according to claim 3, wherein said filter comprises a 0.45 $\mu$m filter.

16. An organ support system adapted for use with a patient comprising:
    an organ assist device for receiving fluid from the patient and designed to pass said fluid therethrough to modify said fluid;
    a first line having first and second ends, said first end being connected to an outlet of the patient for drawing fluid therefrom and said second end being connected to an input of said organ assist device;

a second line having first and second ends, said first end being connected to an output of said organ assist device, and said second end being connected to an input of said patient to return said fluid having been drawn from said patient and having been modified by said organ assist device;

a third line having first and second ends, said first end being coupled to said organ assist device for drawing a predetermined volume of fluid therefrom, and said second end being coupled to said second line; and a control system for automatically controlling said fluid flow of said patient and measuring a characteristic of said fluid, first system having a closed loop configuration formed by said first line, said second line, and said third line, wherein said control system comprises a primary control module including dual pumps, and an auxiliary control module, said auxiliary control module including means for monitoring pressure of said first line, said second line, and said third line, wherein said auxiliary control module includes means for terminating operation of said system when at least a pressure differential between said third line and said second line is greater than a predetermined value.

17. An organ support system according to claim 16, wherein said control module further comprises a venous pressure module, said venous pressure module including means for monitoring pressure in the second line, and wherein said first line, said second line, and said third line each comprise polyvinylchloride.

18. An organ support system according to claim 6, wherein a flow rate of said anticoagulant is from 1 ml/min to 10 ml/min, and preferably 1 to 3 ml/min.

19. An organ support system adapted for use with a patient, comprising:

a metabolically-active device for receiving fluid from said patient and for modifying said fluid, said device having first and second ends, wherein said device comprises a cell line inserted into a hollow fiber cartridge to form a semi-permeable membrane having an extracapillary space for perfusion of cells included in said fluid therethrough for conversion and modification of said fluid;

a first line having first and second ends, said first end being coupled to said patient for receiving said fluid from said patient, said second end being coupled to said device and allowing said fluid to flow to said device;

a second line having first and second ends, said first end being coupled to said device and said second end being coupled to said patient to return said fluid having been modified by said device;

a third line having first and second ends, said first end coupled to said device and said second end being coupled to said second line;

a filter coupled to said third line for preventing cells detachable from said device from being returned to said patient;

a first pressure detector coupled to said first line;

a plurality of pressure detectors coupled to said third line;

a second pressure detector coupled to said second line; and a control system for monitoring and automatically controlling flow of said fluid, said system having a closed loop configuration formed by said first line, said second line, and said third line, said control system comprising means for continuously maintaining a pressure differential between said third line and said second line, wherein said device has a molecular weight cutoff of between 10,000 to 250,000, and preferably between 60,000 to 80,000.

20. A method for extracorporeally and metabolically modifying a bodily fluid of a patient adapted for use with a metabolically-active device, comprising:

removing said fluid from said patient;

passing said fluid through a device adapted to convert metabolites having a predetermined structure from said fluid, said device having a semi-permeable membrane with an extracapillary space through which cells included in said fluid are perfused to convert said fluid;

withdrawing a flow of fluid from said extracapillary space of said device to determine whether said metabolites having said predetermined structure in said fluid in said extracapillary space have been removed;

monitoring and automatically controlling flow of said fluid to prevent cells detached from said extracapillary space of said device and exceeding a predetermined size from returning to said patient;

returning said fluid to said patient, wherein said device is capable of filtering cells having a molecular weight of between 10,000 and 250,000, and preferably between 60,000 to 80,000; and p1 continuously maintaining a pressure differential between said flow of fluid withdrawn from said extracapillary space of said device and said fluid returned to said patient.

21. An apparatus for extracorporeally and metabolically modifying a bodily fluid of a patient, said apparatus comprising:

means for removing said fluid from said patient;

means for converting metabolites having a predetermined structure from said fluid, said device having a semi-permeable membrane with an extracapillary space through which cells included in said fluid are perfused to convert said fluid;

means for passing said fluid through said converting means;

means for withdrawing a flow of fluid from said extracapillary space of said device to determine whether metabolites having said predetermined structure in said fluid in said extracapillary space have been removed;

means for monitoring and automatically controlling flow of said fluid to prevent cells from said extracapillary space of said device and exceeding a predetermined size from returning to said patient; and means for returning said fluid to said patient, wherein said device is capable of filtering cells having a molecular weight of between 10,000 and 250,000, and preferably between 60,000 to 80,000, wherein said means for monitoring and automatically controlling flow of said fluid comprises means for continuously maintaining a pressure differential between said fluid from said extracapillary space of said device and said fluid returned to said patient.

22. An organ support system according to claim 1, wherein said first line includes means for filtering said fluid drawn from said patient to prevent dysfunctionality of said organ asssist device.

23. An organ support system according to claim 19, wherein said first line includes means for filtering said fluid drawn from said patient to prevent dysfunctionality of said organ asssist device.

24. An apparatus according to claim 21, further comprising means for preventing clogging of said converting means.

25. An organ support system according to claim 1, further comprising means for determining parameters of said fluid flowing in said system.

26. An organ support system according to claim 19, further comprising means for determining parameters of said fluid flowing in said system.

27. A method according to claim 20, further comprising determining parameters of said fluid flowing in said system.

28. An apparatus according to claim 21, further comprising means for determining parameters of said fluid removed from said patient.

29. An organ support system adapted for use with a patient, comprising:
- an organ assist device for receiving fluid from the patient and designed to pass said fluid therethrough to modify said fluid, said organ assist device comprising a cell line inserted into a hollow fiber cartridge having a semi-permeable membrane and forming an intracapillary space for passing said fluid therethrough and an extracapillary space for perfusion of cells of said fluid therethrough for conversion and modification of said fluid;
- a first line having first and second ends, said first end being connected to an outlet of the patient for drawing fluid therefrom, and said second end being connected to an input of said organ assist device;
- a second line having first and second ends, said first end being connected to an output of said organ assist device, and said second end being connected to an input of said patient to return said fluid having been drawn from said patient and having been modified by said organ assist device;
- a third line having first and second ends, said first end being coupled to said organ assist device for drawing a predetermined volume of fluid therefrom, and said second end being coupled to said second line; and
- a control system for automatically controlling said fluid flow of said patient and measuring a characteristic of said fluid, said system having a closed loop configuration formed by said first line, said second line, and said third line, said control system comprising means for continuously maintaining a positive pressure gradient from said intracapillary space to said extracapillary space.

* * * * *